(12) United States Patent
Meinhart et al.

(10) Patent No.: US 11,821,623 B2
(45) Date of Patent: Nov. 21, 2023

(54) MICROFLUIDIC-BASED APPARATUS AND METHOD FOR VAPORIZATION OF LIQUIDS

(71) Applicant: Numerical Design, Inc., Santa Barbara, CA (US)

(72) Inventors: Carl D. Meinhart, Santa Barbara, CA (US); Brian Piorek, Santa Barbara, CA (US); Nicholas B. Judy, Santa Barbara, CA (US)

(73) Assignee: Numerical Design, Inc., Santa Barbara, CA (US)

( * ) Notice: Subject to any disclaimer, the term of this patent is extended or adjusted under 35 U.S.C. 154(b) by 0 days.

(21) Appl. No.: 17/868,628

(22) Filed: Jul. 19, 2022

(65) Prior Publication Data

US 2023/0086810 A1    Mar. 23, 2023
US 2023/0214550 A9    Jul. 6, 2023

Related U.S. Application Data

(63) Continuation of application No. 16/678,485, filed on Nov. 8, 2019, now Pat. No. 11,408,607, which is a
(Continued)

(51) Int. Cl.
| | |
|---|---|
| *F22B 1/28* | (2006.01) |
| *F24F 6/02* | (2006.01) |
| *A61L 9/03* | (2006.01) |
| *B01B 1/00* | (2006.01) |
| *B05B 7/16* | (2006.01) |
| *G06F 30/20* | (2020.01) |
| *G06F 17/18* | (2006.01) |
| *G06Q 10/0639* | (2023.01) |

(Continued)

(52) U.S. Cl.
CPC ............ *F22B 1/284* (2013.01); *A61L 9/037* (2013.01); *B01B 1/005* (2013.01); *B05B 7/1686* (2013.01); *F24F 6/025* (2013.01); *G06F 17/18* (2013.01); *G06F 30/20* (2020.01); *G06Q 10/0639* (2013.01); *G06F 2111/04* (2020.01); *G06F 2111/10* (2020.01); *G06N 3/042* (2023.01)

(58) Field of Classification Search
CPC ......... H05B 6/06; H05B 6/108; A24F 47/006; A24F 47/004; A24F 47/008; F22B 1/284; F24F 6/025; A61L 9/037; B01B 1/005; B05B 7/1686; G06N 3/042
See application file for complete search history.

(56) References Cited

U.S. PATENT DOCUMENTS

| | | | |
|---|---|---|---|
| 8,369,694 B2* | 2/2013 | Pitz | A61L 9/03 392/394 |
| 9,743,463 B2* | 8/2017 | Laghi | H05B 6/105 |

(Continued)

*Primary Examiner* — Brian W Jennison
(74) *Attorney, Agent, or Firm* — Mark Rodgers

(57) ABSTRACT

Methods and apparatus for vaporizing liquid into the surrounding environment, including directing liquid from a liquid source to a vaporization port where the vaporization port has lateral dimensions varying from 10 um to 300 um, applying heat to the liquid in the vaporization port with an at least one heating element located in thermal communication to the vaporization port, and releasing vaporized liquid from the vaporization port into the surrounding environment so that fluid is transported through the depth of the structure.

16 Claims, 24 Drawing Sheets

Related U.S. Application Data continuation of application No. 14/885,822, filed on Oct. 16, 2015, now Pat. No. 10,502,409.

(60) Provisional application No. 62/081,476, filed on Nov. 18, 2014, provisional application No. 62/066,320, filed on Oct. 20, 2014.

(51) Int. Cl.
  *G06F 111/04* (2020.01)
  *G06F 111/10* (2020.01)
  *G06N 3/042* (2023.01)

(56) References Cited

U.S. PATENT DOCUMENTS

| | | | |
|---|---|---|---|
| 2016/0007653 A1* | 1/2016 | Tu | F22B 1/284 29/890.07 |
| 2017/0106113 A1* | 4/2017 | Meinhart | A61L 9/037 |

\* cited by examiner

Interposer

Interposer (cross section view)

Step 1 – Heater metal deposition 700

Step 2 – Hard mask deposition 701

Step 3 – Backside hard mask and glass etching 702

Step 4 – Topside hard mask and glass etching 703

Step 5 – Hard mask removal 704

Step 1 – Heater metal deposition 710

Step 2 – Hard mask deposition 711

Step 3 – Hard mask and substrate etching 712

Step 4 – Hard mask removal 713

Step 5 – Adhesion layer deposition and wafer bonding 714

Step 6 – Bonded assembly 715

```
Directing a liquid from a Liquid Source to a
Vaporization Port 801
```
↓
```
Applying heat to the liquid in the Vaporization Port
with a Heating Element to vaporize the liquid 802
```
↓
```
Releasing vaporized liquid from the
Vaporization Port into the Surrounding
Environment so that fluid is transported
through the depth of the Structure 803
```

FIG. 8

MICROFLUIDIC-BASED APPARATUS AND METHOD FOR VAPORIZATION OF LIQUIDS

CROSS-REFERENCE TO RELATED APPLICATIONS

This application claims priority to U.S. patent application Ser. No. 16/678,485, filed Nov. 8, 2019, which in turn claims priority to U.S. patent application Ser. No. 14/885,822, filed Oct. 16, 2015 which in turn claims priority to Provisional applications; Ser. No. 62/066,320 filed Oct. 20, 2014 and Ser. No. 62/081,476 filed Nov. 18, 2014, all of which are incorporated by reference in their entirety.

BACKGROUND

This specification relates to an apparatus and methods for vaporizing liquids and in particular a vaporizer providing well-controlled spatial distributions of vapor, with controlled and accurate dosage of vapor, with well-controlled vaporization temperature profiles, and with high thermodynamic efficiency.

Vaporizers, such as e-cigarettes, humidifiers and other personal as well as medical vaporizers and fragrance vaporizers are becoming increasingly common. Many such vaporizers rely on techniques which have been prevalent for many years. Such vaporizers may benefit from new design approaches and modern fabrication capabilities.

SUMMARY

In some embodiments an apparatus may be microfabricated using batch fabrication techniques, the devices can be manufactured to be nearly identical from device to device. Microfabrication allows the devices to be manufactured in large volumes with high unit-to-unit reproducibility and low per-unit cost.

In some embodiments, a vaporization apparatus may be provided that may be placed within a surrounding environment to vaporize liquid into the surrounding environment, including at least one liquid source, at least one vaporization port that may be formed in a structure, with lateral dimensions varying from 10 um to 300 um, that may be in fluid communication with the liquid source and the surrounding environment, and at least one heating element that may be in thermal communication to the at least one vaporization port.

In some embodiments, the fluid communication between the liquid source and the surrounding environment may occur throughout the depth of the apparatus, so that fluid is transported through the depth of the structure.

In some embodiments, the structure may include a thin structural region, with a thickness varying from 1 um to 100 um, and in some embodiments 10 um to 100 um.

In some embodiments, a protective layer may be formed on the structure that surrounds the heating element.

In some embodiments, the protective layer may include deposited glass.

In some embodiments, a surface coating may be formed on the structure but may be masked from forming on the walls of the vaporization ports.

In some embodiments, the surface coating may include fluoropolymers.

In some embodiments, the surface coating may include silicon nitride.

In some embodiments, at least one of a bead or particle wicking structure may be located in at least one of the liquid source region(s) of the structure or within the ports.

In some embodiments, at least one of the beads or particles may have dimensions of 10 um to 300 um or as much a 1 mm.

In some embodiments, at least one of the beads or particles may comprise a hydrophilic surface.

In some embodiments, at least one of the beads or particles may comprise a hydrophobic surface.

In some embodiments, at least one of the beads or particles may be sintered.

In some embodiments, at least one of the beads or particles are comprised of glass.

In some embodiments, the heating element may be a thin-film resistive heating element.

In some embodiments, the resistances of the resistive heating elements may be varied to provide a controlled thermal distribution.

In some embodiments, the resistive heating elements may be electrically connected in parallel and series combination.

In some embodiments, a method may be provided for vaporizing liquid into the surrounding environment, including directing liquid from a liquid source to a vaporization port, wherein the vaporization port may have lateral dimensions varying from 10 um to 300 um, applying heat to the liquid in the vaporization port with at least one heating element located in close proximity to the vaporization port, and releasing vaporized liquid from the vaporization port into the surrounding environment.

In some embodiments, during operation, liquid may continually flow from the liquid source to the vaporization port, may change phase from liquid to vapor, and the vapor may continuously flow from the vaporization port to the surrounding environment.

In some embodiments, fluid may flow through the depth of the structure from the liquid source to the surrounding environment.

In some embodiments, a thin structural region may substantially confine thermal energy to close proximity of the at least one heating element and the at least one vaporization port.

In some embodiments, the thin structural region may reduce thermally-induced stresses that may occur in close proximity to the at least one heating element and the at least one vaporization port.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIG. 8 shows a flowchart depicting a method of an illustrative embodiment.

DETAILED DESCRIPTION

Figure 1:
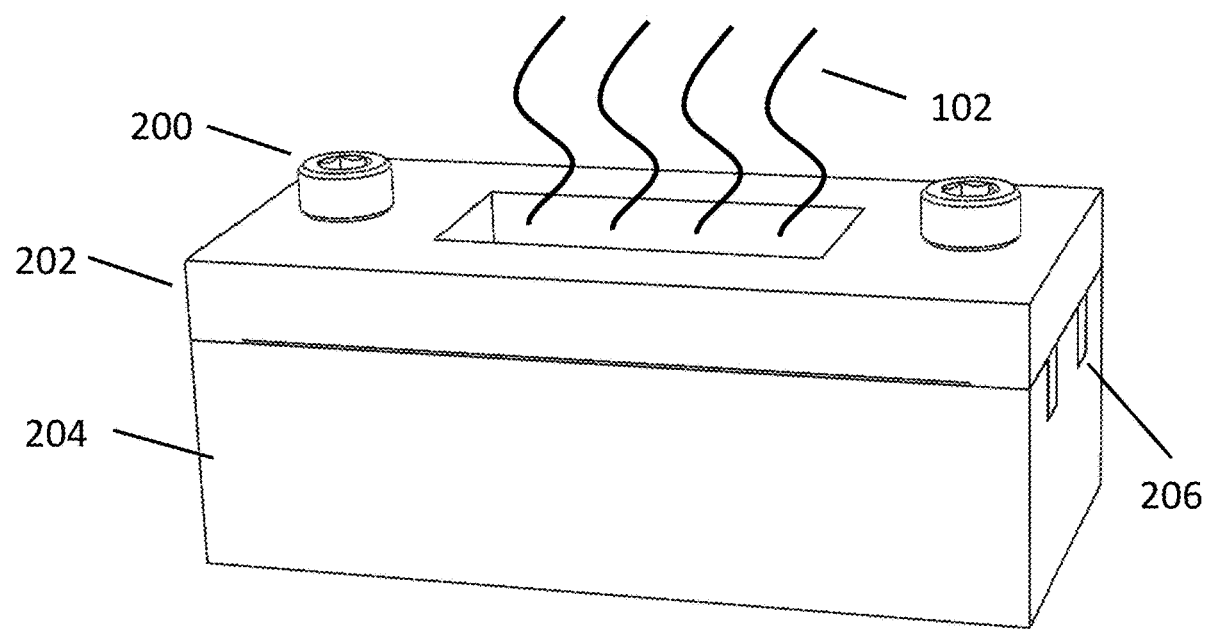
FIG. 1 shows a perspective view of the apparatus of an illustrative embodiment.

Generally described, aspects of the present disclosure relate to vaporizers produced using fine scale microfabrication techniques for both the structure and heating element. Microfabrication may include patterning, etching, deposition, injection and related processes on such materials as glass, metals, plastics and crystalline materials such as silicon and silicon derivatives. Heating elements may include electronic circuits made from electrical components including resistors, capacitors, transistors, logic element and the like which also may be fabricated onto application specific circuits and/or made up of discrete components in any combination.

One or more embodiments described herein may provide well-controlled heating, thus minimizing the effect of the liquid to become excessively hot, thus minimizing undesirable chemical reactions that produce undesirable and/or harmful chemical reaction products.

One or more embodiments described herein may provide vaporization devices manufactured in a highly controlled manner, thus reducing significant variation from unit to unit, and thereby reducing variation in performance.

One or more embodiments described herein may provide vaporizers which are thermodynamically efficient, and less bulky in size.

Microfluidic vaporizers disclosed here may be used to provide efficient vaporization of low-volatility liquids for a large range of applications, including fragrance distribution, medical vaporization, vaporized drug delivery, chemical distillation, chemical-reaction control, aromatics, waxes, scented waxes, air sterilization, theatrical smoke, fog machines, aroma therapy, essential oils, personal vaporizers, chemical vapor or aerosol detector calibration devices, smoking articles, and electronic cigarettes.

Vaporization devices are a general class of devices used to create vapors or aerosols from liquids. Vaporizers have many applications, including but not limited to: fragrance distribution, medical vaporization, vaporized drug delivery, chemical distillation, chemical-reaction control, aromatics, waxes, scented waxes, air sterilization, theatrical smoke, fog machines, aroma therapy, essential oils, personal vaporizers, smoking articles and electronic cigarettes, among others.

The present disclosure describes embodiments, where the vaporization device is microfabricated using modern microfabrication techniques, including lithography, deposition and etching techniques. Such techniques may be applied advantageously to vaporizer design. For example, an embodiment could have micron-scale precision components. In yet other embodiments, the disclosed apparatus and methods could be compatible with injection molded plastics. In an embodiment, the vaporization apparatus and method could have similar geometries from unit to unit. Furthermore, an embodiment could be produced at a low cost in high production volume.

The current application discloses an embodiment which may provide desirable performance improvements. For example in an embodiment, the micron-scale precision of the components allows for accurate dosing of a vaporized material, and precisely-controlled temperature, which can eliminate overheated regions that produce undesirable chemical reaction products. In additional embodiments, the apparatus can be designed to minimize parasitic heat transfer to the substrate, surrounding environment or interposer. In some embodiments, the apparatus can be made very small, planar and highly portable. The micron-scale features can improve the thermodynamic efficiency of the apparatus and method, and could have minimal energy requirements. In yet another embodiment, the vaporization ports could be individually addressed and activated in a controlled fashion, so that a chemical reaction front or precise release of particular chemicals based on time and individual position within the array of vaporization ports could be established.

FIG. 1 shows a schematic of a vaporization unit for an illustrative embodiment. The unit comprises a microfluidic device (not shown) for vaporization that is contained within a plastic housing commonly referred to as an interposer body 204. The interposer body 204 can be mated to an interposer retaining ring 202 by bolt 200. An electrical interconnect 206 can be used to deliver electrical energy. Vapor 102 can emanate from the apparatus.

Figure 2A:
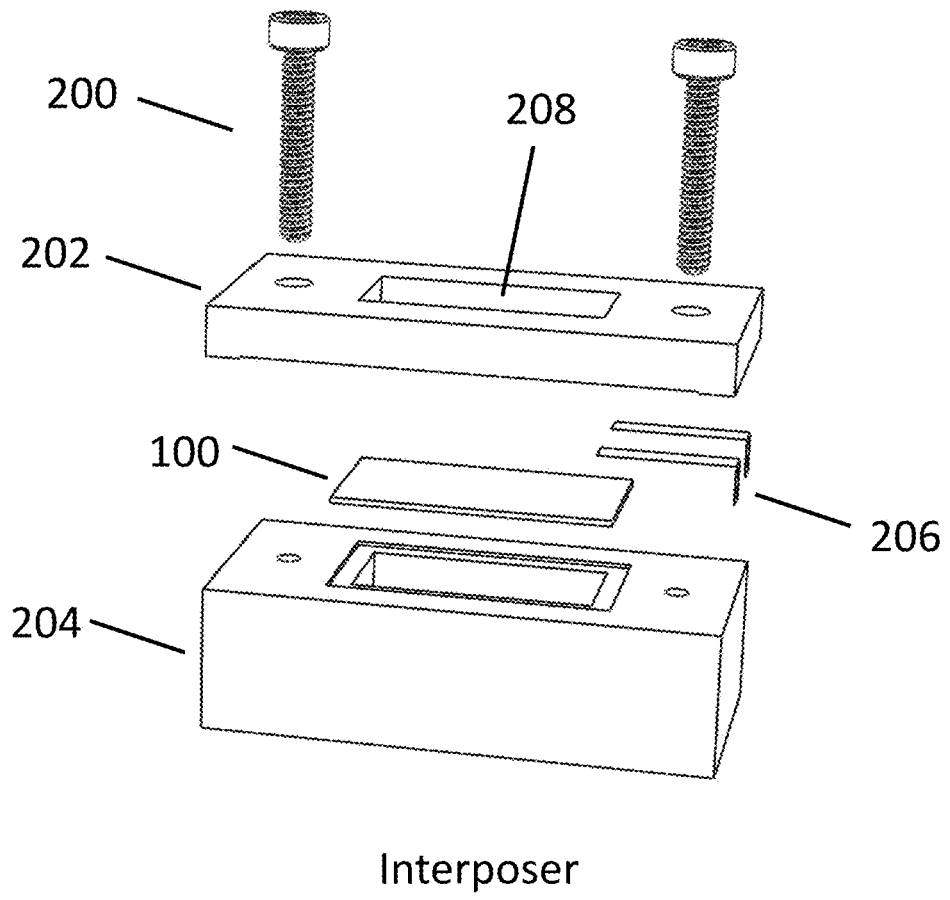
FIGS. 2a and 2b show an exploded view and a cross sectional view of an illustrative embodiment.
Figure 2B:
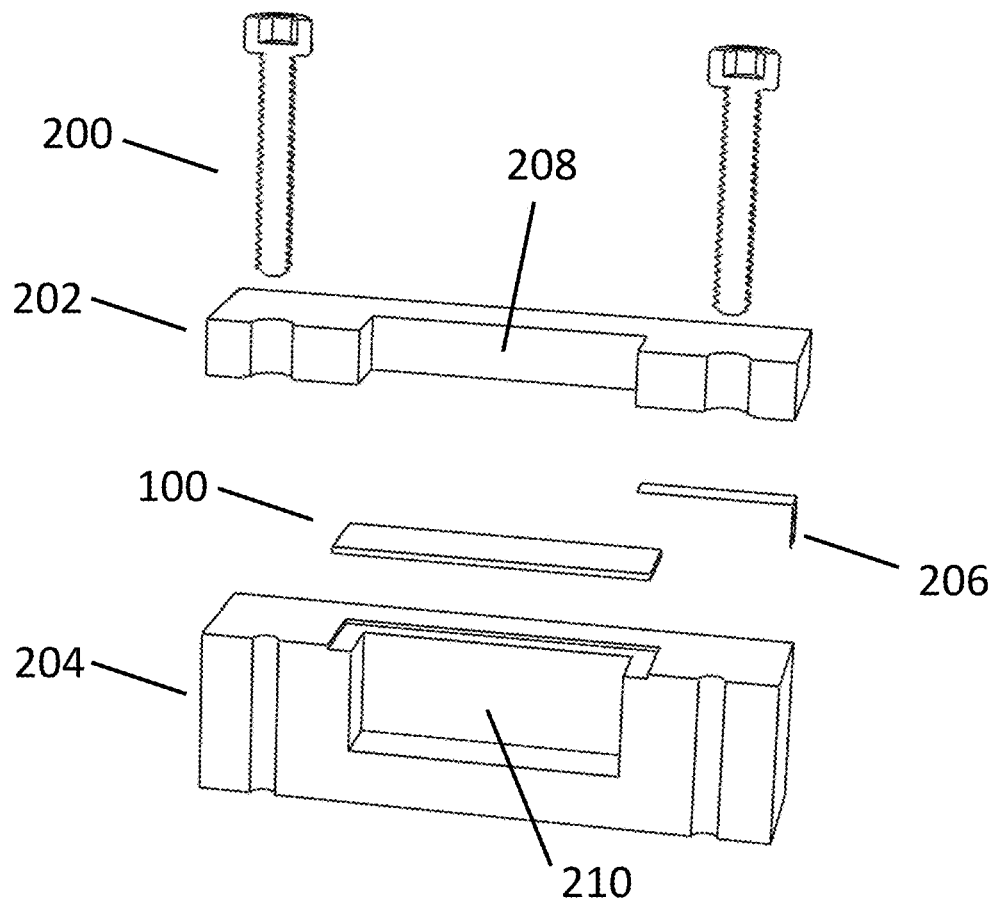

FIG. 2a and FIG. 2b depict an exploded view of an embodiment. The interposer body 204 and interposer retaining ring 202 are in communication with vaporizing structure 100. Vaporizing structure 100 can be comprised of a microfluidic chip. Vapor region 208 is in communication with structure 100 and allows vapor to emanate from microfluidic device structure 100. Electrical interconnect 206 is in electrical communication with microfluidic device structure 100.

In an embodiment, the interposer body 204 is comprised of injection-molded plastic and designed for ease of assembly. In other embodiments, the interposer body 204 can be 3-D printed, machined, and can be made from a large selection of plastics, metals, fiberglass, composites, ceramics, or other structural materials.

Electrical interconnects 206 allow the device to be connected an electronic control unit (not shown). In an embodiment, the electrical interconnects could be formed from a conducting tape, flat wire, wire bond, bump bond, solder bond or other connection process.

In one illustrative embodiment, the overall dimensions of the plastic housing could be nominally 4 mm×6 mm×12 mm. In other embodiments, the plastic housing could range in dimensions from less than 0.1 mm to more than 100 mm, and could contain one or more microfluidic devices.

Figure 3A:
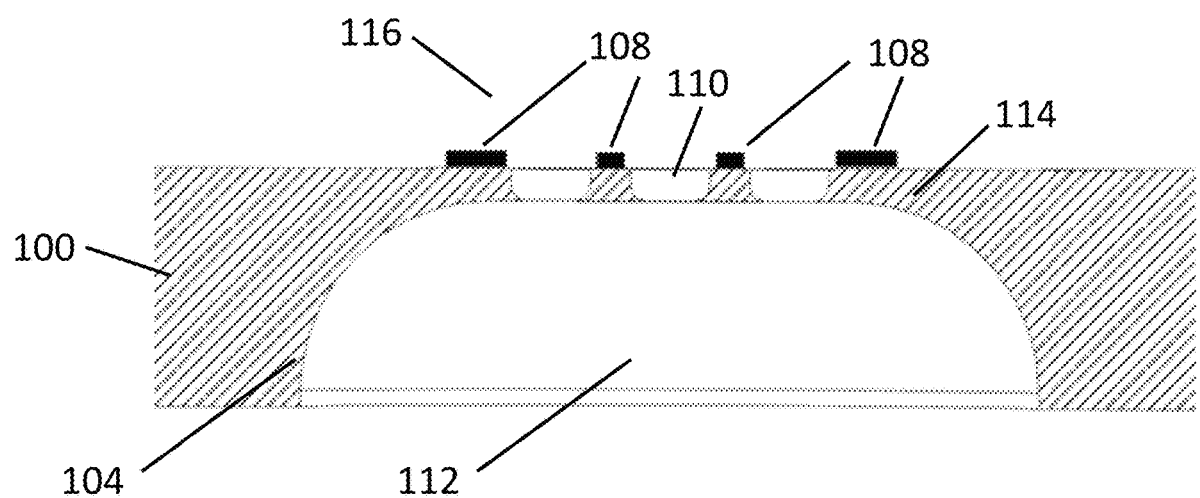
FIGS. 3a and 3b show a profile view, and a perspective view of an illustrative embodiment.
Figure 3B:
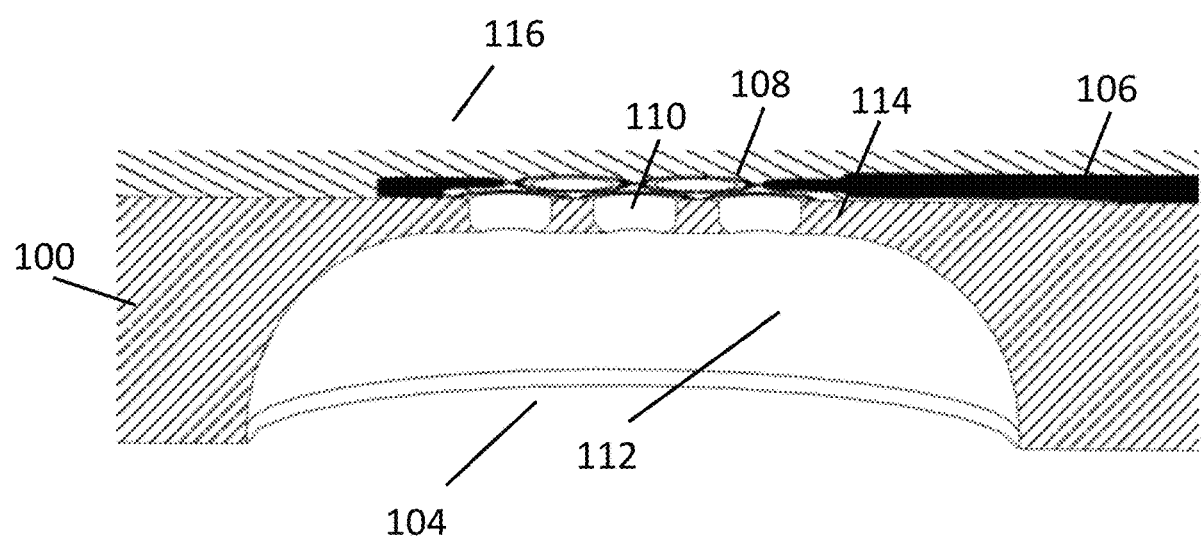

FIG. 3 shows a cross-section view of the apparatus depicting the various components of an embodiment. FIG. 3a is a side view and FIG. 3b is tilted slightly to show the top surface. The surrounding environment 116 is above the structure 100. Vaporization ports 110 are formed in the structure and are in fluid communication with the liquid source 112 and the surrounding environment 116. Liquid source 112 is a region of the structure in fluid communication with a liquid reservoir, not shown and with the vaporizer port region of the apparatus. A heating element 108 is in thermal communication with the vaporization port 110 and located on a structural region 114, which in some embodiments may be a thinned region of the structure. Heating element 108 is in electrical communication with electrode lead 106. A vaporization cluster 104 is region that contains a collection of vaporization ports 110 that are in close proximity with one or more vaporization ports 110. In some embodiments, liquid source 112 may be a wax or otherwise solid phase material which exists in the liquid phase near vaporization port 110 due to the addition of heat.

In the current context, thermal communication refers to the ability to readily transfer thermal energy through heat conduction from one region of the apparatus to another region of the apparatus. In some embodiments, thermal communication occurs between two regions when the distance between those regions is substantially smaller than other dimensions in the apparatus, or the thermal conductivity of the material connecting the two regions is equal to or larger than the thermal conductivity of materials in other regions of the apparatus. In some embodiments heating element 108 can be in thermal communication with vaporization port 110, because the lateral distance between the two components could range between 5 um to 100 um. In some embodiments, the distance between heating element 108 and vaporization port 110 could range from 0.5 um-1 mm. This distance could be substantially smaller than other dimensions of the apparatus. In an illustrative embodiment, the depth of structure 100 could range between 10 um-1000 um, and the lateral size of structure 100 could range between 1 mm-100 mm or even larger.

FIG. 3a shows an illustrative embodiment, where the thin structural region 114 is nominally 40 um thick. In some embodiments the thin structural region 114 can range from 1 um to 100 um. In yet other embodiments, the thickness of the thin structural region 114 can vary from 1 um to 1000 um.

FIG. 4 shows profile views of illustrative embodiments. The surrounding environment 116 is above the structure 100. A vaporization port 110 is formed in the structure 100 and is in fluid communication with the liquid source 112 region and the surrounding environment 116. A heating element 108 is in close proximity to vaporization port 110. In an illustrative embodiment, heating element 108 could be located within 5-100 um (or 0.5 um to 1 mm) of vaporization port 110. In an illustrative embodiment, heating element 108 is located within 0.5-1000 um. Meniscus 118 defines the vapor and liquid interface. A thin structural region 114 can be formed in structure 100. A contact area 140 can be formed between the liquid from the liquid source 112 and the thin structural region 114.

In some embodiments the thin structural region 114 could be adjacent to the vaporization ports 110 and the heating elements 108, which could minimize parasitic heat transfer to the bulk structure 100. In some embodiments meniscus 118, which separates the liquid in the vaporization port and the surrounding environment, could have curvature, which could create a difference in pressure between the liquid source 112 and the surrounding environment 116. In some embodiments, there is significant contact surface area 140 between the thin structural region 114 and the liquid contained in a vaporization port 110 and the liquid source 112.

Figure 4A:
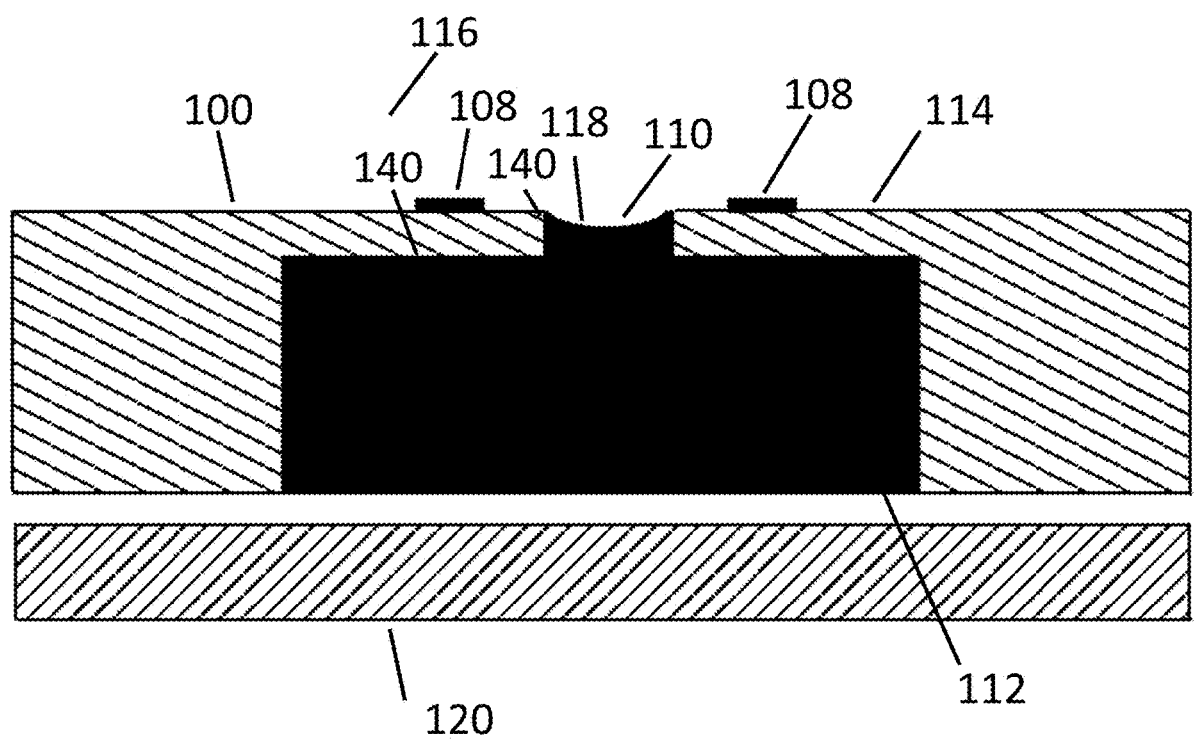
FIGS. 4a, 4b and 4c show profile views of the apparatus depicting components of an illustrative embodiment.

FIG. 4a depicts an illustrative embodiment where an optional bulk heater or cooler 120 could be located in thermal communication to liquid source region 112, to control the bulk temperature of the liquid source 112.

Figure 4B:
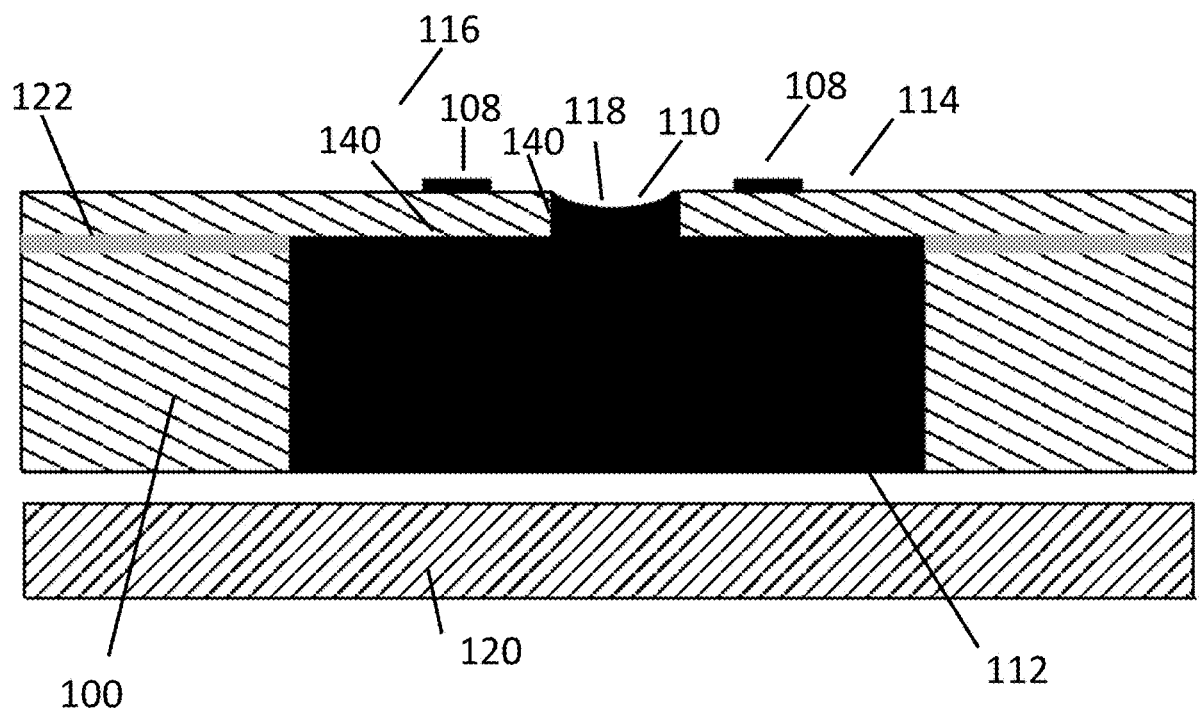

FIG. 4b depicts an illustrative embodiment where structure 100 is bound to thin structural region 114 with structural bond 122.

Figure 4C:
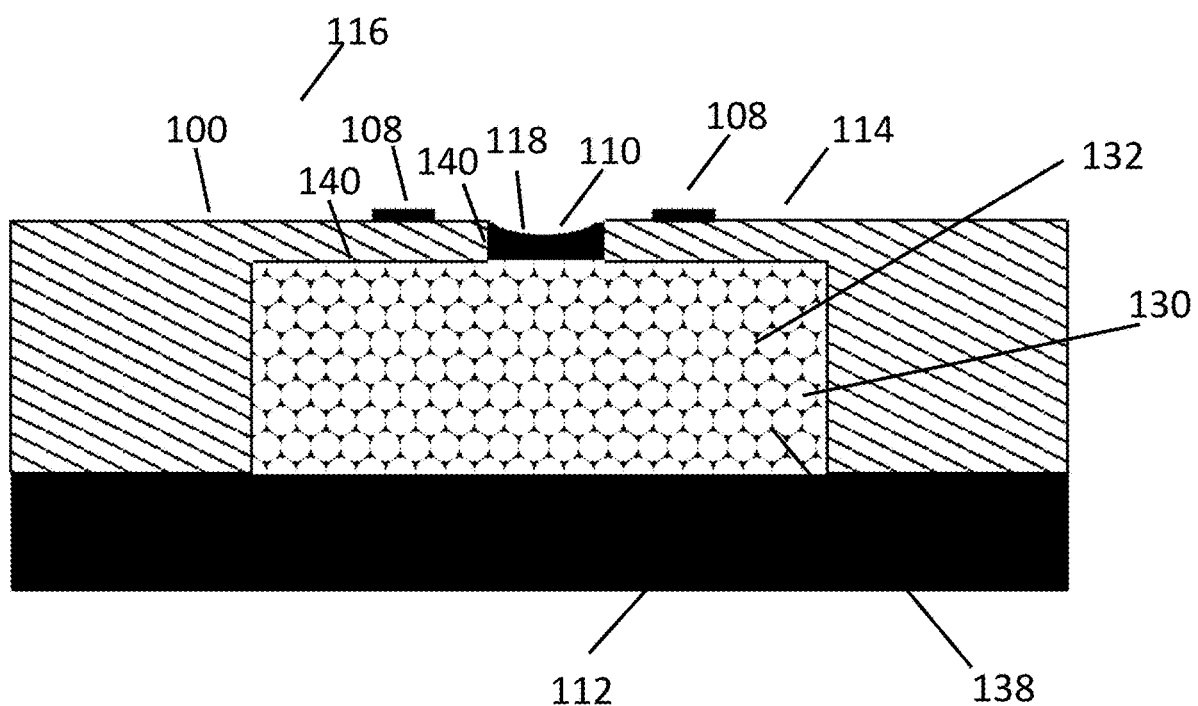

FIG. 4c shows a profile view of the apparatus depicting the various components of another illustrative embodiment. The surrounding environment 116 is above the structure. Vaporization ports 110 are formed in the structure 100 and are in fluid communication with the liquid source 112 and the surrounding environment 116. A heating element 108 is in thermal communication with the vaporization port 110 and located on a thin structural region 114. In an embodiment, particles or beads 130 form a wicking structure located in all or part of the liquid source region 112 and optionally located in the vaporization port 110 as well, and at least in the region adjacent to the vaporization port 110. In an embodiment, the particles or beads 130 may be hydrophilic. In an embodiment, the particles or beads 130 may be hydrophobic, or may be a hydrophilic/hydrophobic combination. In an embodiment, hydrophilic particles or beads 130 may be formed from glass or other materials. In an embodiment, the particles or beads 130 may be optionally sintered 132 or joined together by some other manner. In an embodiment, the particles or beads form small interstitial regions 138 that enhance the effect of the hydrophilic or hydrophobic surface properties of the beads or particles 130. In an embodiment, the particles or beads 130 could range in size from ten nanometers to 10 millimeters. In an embodiment, the particles or beads could range in size from 1 micrometer to 1 millimeter. In an embodiment, the particles or beads 130 could range in size from 10 micrometers to 300 micrometers.

Figure 5:
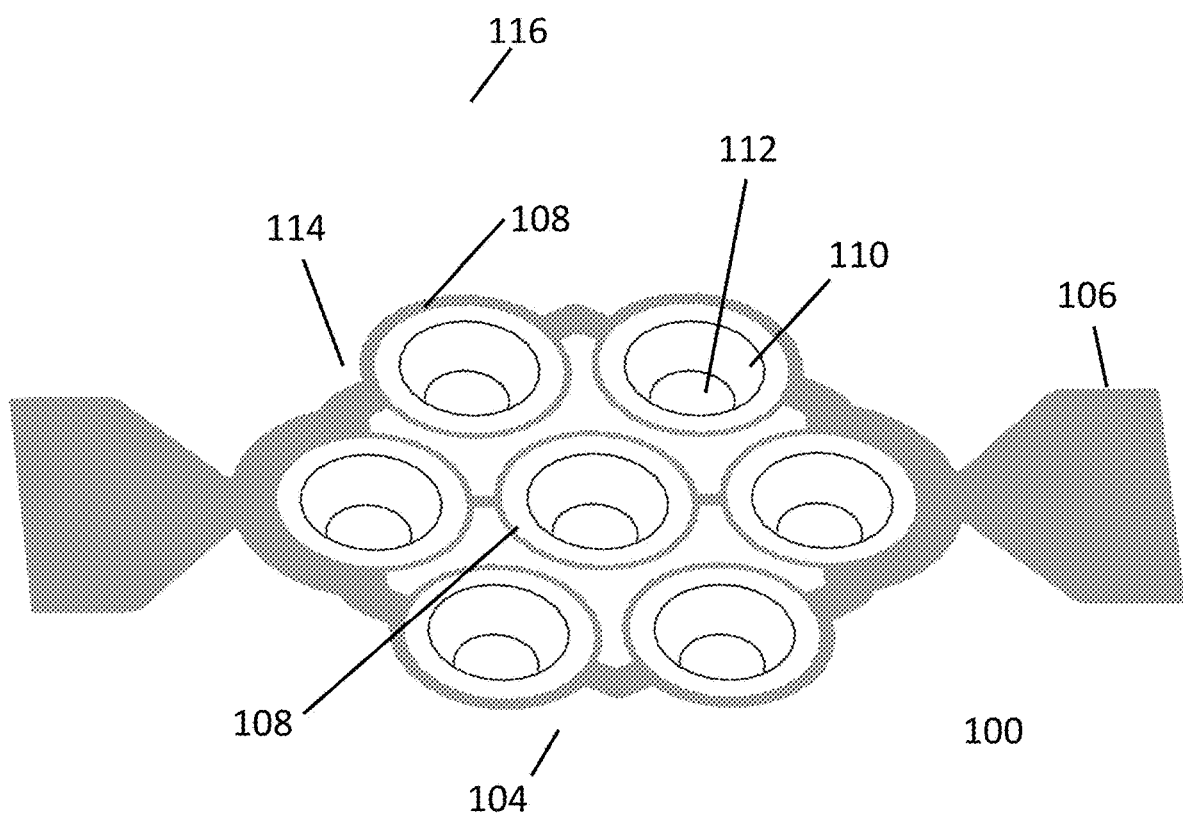
FIG. 5 shows a top view of the apparatus depicting some of the major components of an illustrative embodiment.

FIG. 5 shows a top view of the apparatus depicting some of the major components of an embodiment. Vaporization ports 110 are formed in the structure 100 and are in fluid communication with the liquid source region 112 and the surrounding environment 116. A heating element is in thermal communication with the vaporization port 110 and located on a thin structural region 114. In an embodiment, the heating element 108 is a thin film resistive heating element. In an embodiment the thin film heating element is configured into three parallel circuits, which further form a parallel circuit surrounding each vaporization port.

FIG. 5 shows a detailed view of an example embodiment where a single vaporization cluster 104, has a lateral dimension of approximately 900 um, contains seven vaporization ports 110, with lateral dimensions of 60 um-150 um, and heating elements 108 in thermal communication with the vaporization ports 110 such that heat produced by the heating elements 108 is transported to the region of the vaporization ports 110 which contacts the fluid 112 and contact area 140. In illustrative embodiments, the vaporization ports can range in size from 10 um to 300 um in lateral dimension, and in other embodiments range from 1 um to 1000 um. In illustrative embodiments the vaporization cluster could range in lateral dimensions from 10 um to 100 mm. In illustrative embodiments the vaporization cluster could range in lateral dimensions from 100 um to 10 mm The width of the heating elements 108 can be optionally configured with varying widths and thickness, or varying materials to produce a desired Joule heating profile. In some embodiments a desired heating profile may be chosen to provide uniform vaporization of a working fluid, while avoiding excessive heating from undesirable hot-spots. In some embodiments, 0.01 to 500 Watts of heat may be delivered to the fluid 112 to produce vapor 102. In other embodiments, 1 to 50 Watts of heat may be delivered to the fluid 112 to produce vapor 102.

In some illustrative embodiments, a hierarchy of resistive heating elements being connected in parallel (as depicted in FIG. 5) may have certain advantages. For example, the electrical resistance of metals can increase with increasing temperature. Therefore, if one element of a parallel circuit has a higher temperature than another element of the parallel circuit, that element could have a higher resistance and force more electrical current through the lower temperature element and thereby increase the Joule heating produced by the lower temperature element. In some embodiments, resistive heating elements connected in parallel could facilitate thermal regulation, which could help mitigate local thermal hot spots.

Figure 6A:
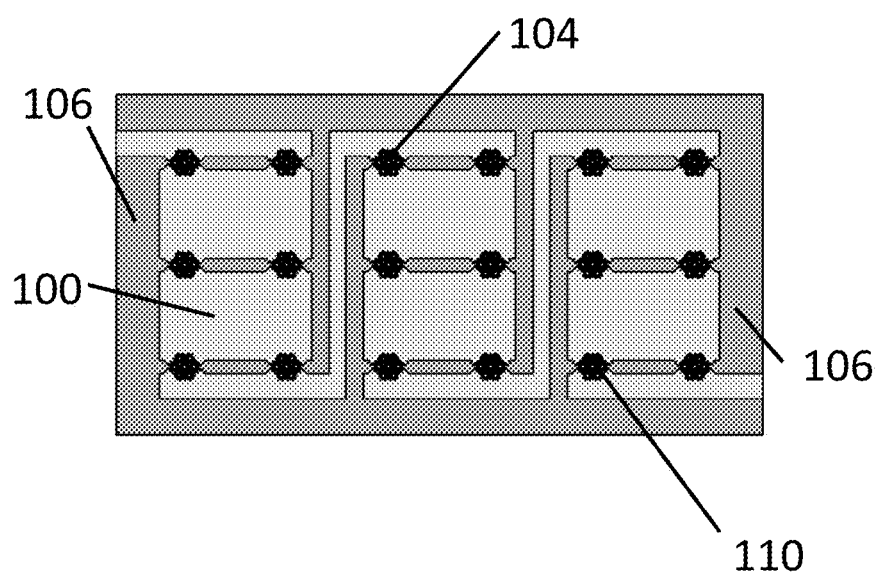
FIGS. 6a and 6b show a schematic of an exemplary microfluidic vaporization chip for an illustrative embodiment that contains 18 vaporization clusters
Figure 6B:
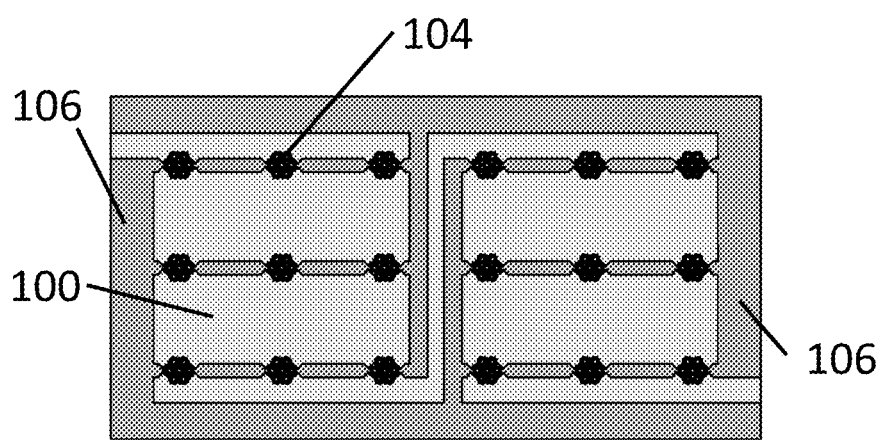

FIGS. 6a and 6b show an overview of a single microfluidic vaporization device structure 100. In an illustrative embodiment a single device structure 100 contains eighteen vaporization clusters 104 with each cluster 104 containing seven vaporization ports 110, for a total of 18×7=126 vaporization ports 110 for this example embodiment. In one example embodiment shown in FIG. 6a, two vaporization clusters 104 are connected by electrode leads 106 in series with nine parallel circuits. In another example embodiment shown in FIG. 6b, three vaporization clusters 104 are connected by electrode leads 106 in series with nine parallel circuits.

In other illustrative embodiments, the clusters could be connected in various series and/or parallel configurations, individually addressable, or other electrical wiring scheme. In an example embodiment, the microfluidic device structure 100 is 4 mm×10 mm in lateral dimension and 0.3 mm thick. In an example embodiment, the microfluidic chip is fabricated from glass, but for other embodiments, it could be fabricated from plastic, silicon, titanium, metals, ceramics, PDMS, polymers, fiberglass, composites, or other materials.

Joule heating from a resistive element can be described by $Q=V^2/R$, where Q is the Joule heating power, V is the voltage drop across the resistive element and R is the electrical resistance of the element. As temperature increases, the electrical resistance of metals increases. If the voltage drop is constant, the amount of Joule heating will decrease with increasing temperature. Therefore, in an embodiment, it can be advantageous to have parallel circuits. If one branch of the parallel circuit has a higher temperature than another branch of the circuit, the branch with a higher temperature will have a higher resistance, and will therefore produce less Joule heating. In an embodiment with parallel resistive heaters, the various branches of the circuit may have self-regulating properties, that may help to regulate Joule heating that may help to maintain more uniform temperatures in comparison to the reduced uniformity which could occur using non-parallel circuit configurations.

In some embodiments, parallel resistive heaters could be configured with different resistance in each branch. In some embodiments, resistance of the heating elements could be modified by using different materials, different depths, different lengths, and/or different widths. In some embodiments, branches of parallel resistive heaters can have different resistances that could be optimized to produce desirable and well-controlled temperature distributions. In some embodiments, uniform temperature distributions may be desirable. In some embodiments, non-uniform temperature distributions may be desirable.

In some embodiments a hierarchical combination of parallel and resistive heating elements 108 can be judiciously chosen to provide desired heating profiles, and self-regulating heating elements.

Figure 7A:
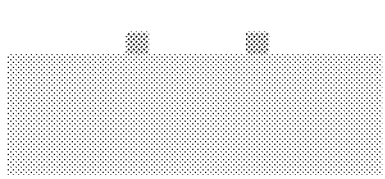
FIGS. 7a and 7b show examples of microfabrication process flows for device fabrication for an illustrative embodiment.
Figure 7A:
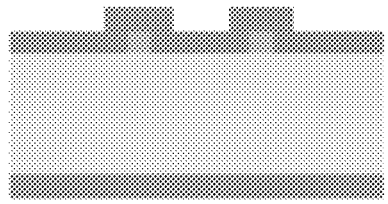
Figure 7A:
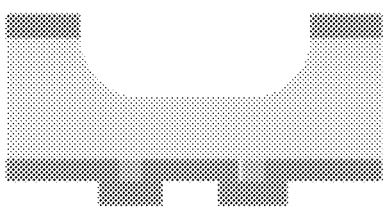
Figure 7A:
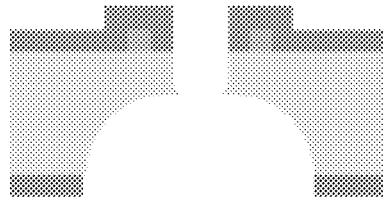
Figure 7A:
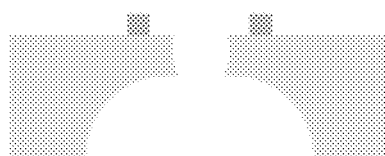

FIG. 7a shows an example for a microfabrication process flow for device fabrication for an embodiment, which consists of five processing steps using a single structure. In an illustrative embodiment, the structure 100 could be made from a 300 μm thick glass substrate from Schott (D263T-eco, AF32-eco or MEMpax). The glass substrate could be formed from a variety of materials and thicknesses ranging from 1 um to 10 mm. A photoresist could be patterned and metal (for example, titanium and platinum) could be deposited for the electrode leads and heating elements (Step 1—Heater metal deposition 700). After photoresist and metal liftoff, a hard mask film (for example, chromium/gold, aluminum or amorphous silicon) could be deposited on both sides of the substrate (Step 2—Hard mask deposition 701). On the backside, photoresist could be patterned and the hard mask could be etched (wet or dry) followed by the glass being optionally wet etched down to roughly half the substrate thickness (Step 3—Backside hard mask and glass etching 702). On the frontside, the vaporization port 110 could be patterned in close proximity (which could range between 5 um to 100 um, or 0.5 um to 1 mm) to the heater element 108 and a hard mask could be etched, followed by optional wet etching of the glass. At the same time, the backside could optionally be further etched since it could optionally be exposed, and a via (or through hole) could be created (Step 4—Topside hard mask and glass etching 703). This could allow the vaporization port 110 to be in fluid communication with the liquid source 112 and the surrounding environment 116. Finally, the hard mask could be removed from both sides, and the substrate could then be diced (Step 5—Hard mask removal 704).

A variety of nanofabrication and microfabrication equipment could be used to fabricate some embodiments of the vaporization device. The fabrication may include numerous deposition tools such as electron beam deposition, which could be used for the heating element, and plasma enhanced chemical vapor deposition (PECVD), which could be used to deposit the hard masks. In some embodiments, wet chemistry benches could be used for a variety of etch chemistries, including hydrofluoric acid etching of glass. Dry etching could also be used for isotropic etches in certain materials such as inductively coupled plasma reactive ion etching (ICP-RIE). Furthermore, in some embodiments, a photolithography mask aligner capable of backside alignment, such as the SUSS MA-6, could be used to pattern and align the features from front to back.

Figure 7B:
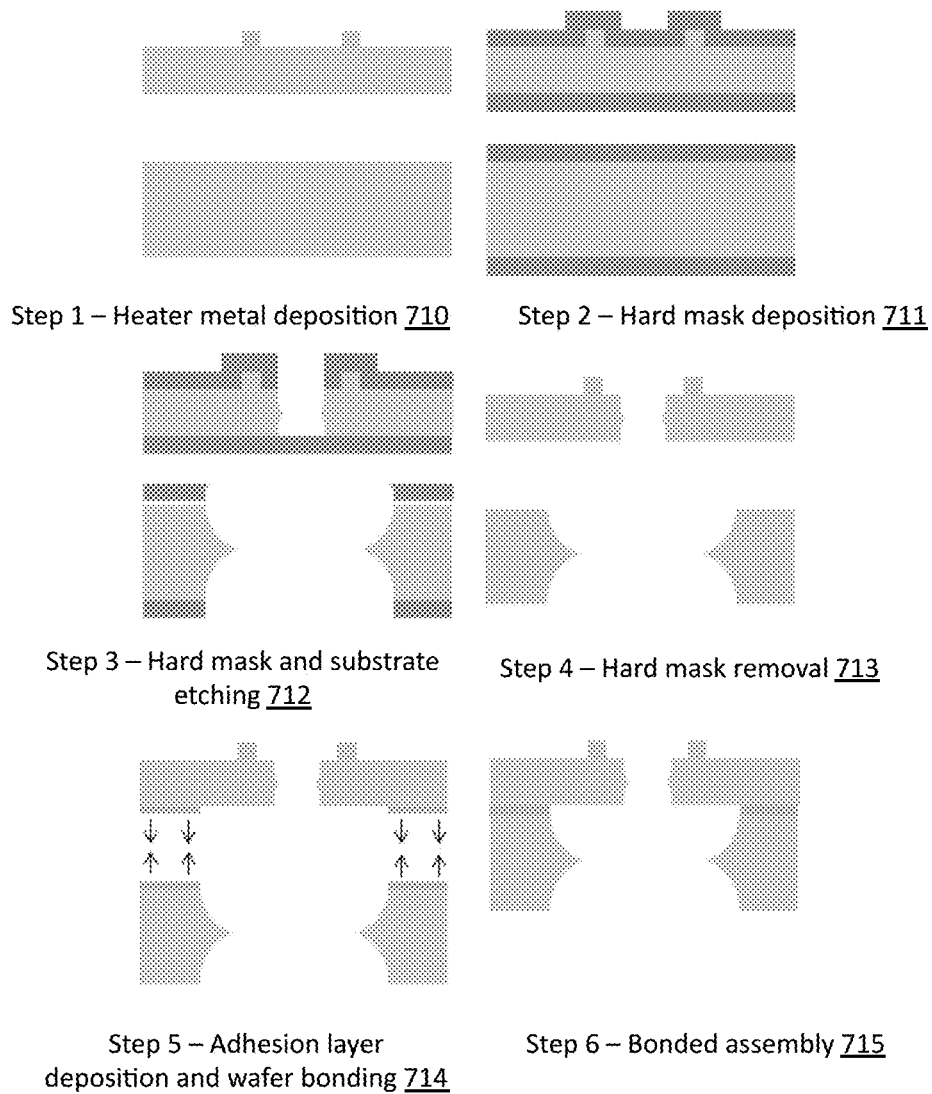

FIG. 7b shows an illustrative for a microfabrication process flow for device fabrication for an illustrative embodiment shown FIG. 4b, which includes six processing steps using structural element 100 and thin structural region 114 (i.e. two initially separate structures). This embodiment could be extended to two or more (i.e. multiple) structures, which could be bonded with structural bond 122 (shown in FIG. 4b) using one or more bonding techniques.

The fabrication process could use 100 um, 300 um, or even 500 um thick glass substrates to form structure 100. Embodiments could use 1 um to 10 mm thick substrates for thin structural region 114 (shown in FIG. 4b), and the substrates could encompass a variety of materials, such as glass, titanium, aluminum, sapphire, silicon carbide, diamond, ceramics, metals, silicon, and the like.

Two different thicknesses of substrates could be used. For example one substrate could be 100 um (i.e. a relatively thin)

substrate and another substrate could be 300 um (i.e. a relatively thick) substrate, which could allow for significantly flexibility in feature sizes during optional wet etch processes. Referring to FIG. 7B, a 100 um thick substrate could be patterned with photoresist and metal could be deposited for the heating element (Step 1—Heater metal deposition 710). An additional metal deposition step could be optionally used for the electrode leads. For example, in an embodiment, gold contacts could be optionally patterned at the chip connections.

In one embodiment, after photoresist and metal liftoff, a hard mask film could be deposited on both sides of the thin substrate (Step 2—Hard mask deposition 711) and the thick substrate. Photoresist could be patterned on both sides of the substrates to expose regions adjacent to the heating element on the thin substrate and the thick substrate. The hard masks could be etched, followed by the substrates being etched down to half the thickness of the substrates on each side, creating a through hole (i.e. a via through the chip) (Step 3—Hard mask and substrate etching 712), which could provide fluid communication for the vaporization port 110 with the liquid source 112 and fluid communication with the surrounding environment 116.

In this embodiment, the hard mask could then be removed from both sides of the substrates (Step 4—Hard mask removal 713). Depending on the bonding technique, an adhesion layer could optionally be deposited either on the back side of the thin substrate, the top side of the thick substrate, both, or neither. Furthermore, in some embodiments, appropriate cleaning and surface preparation could be applied to the two substrates and they could be bonded together using a variety of well-known bonding techniques (Step 5—Adhesion layer deposition and wafer bonding 714). In some embodiments, the bonded assembly could then be diced into smaller individual units (Step 6—Bonded assembly 715).

FIG. 8 shows a flowchart depicting a method of an embodiment, which involves directing a liquid from a liquid source to a vaporization port 801, and applying heat to the liquid in the vaporization port with a heating element located in close proximity to the vaporization port to vaporize the liquid 802 (which could range between 5 um to 100 um, or 0.5 um to 1 mm). In an embodiment, the vaporized liquid is released from the vaporization port into the surrounding environment so that fluid is transported through the depth of the structure 803. In some embodiments, the vaporization port has lateral dimensions ranging from 10 um-300 um. In yet other embodiments, the vaporization port has lateral dimensions ranging from 1 um-1000 um. Liquid could be introduced to the liquid source by directly placing the liquid in the liquid source or by an optional pump or an optional wicking structure wherein the liquid could be transported through capillary action to the liquid source. In an embodiment, electrical energy could be applied to the heating element, and the heating element could be heated through Joule heating (i.e. resistive heating). The thermal energy from the heating element could then be transferred to the thin structural region, which is adjacent to the vaporization port and liquid source. Heat could then be conducted locally into the liquid to heat the liquid to an optimal temperature for vaporization. This temperature could be well controlled so that the liquid is heated sufficiently for vaporization, but does not reach an undesirably high temperature, which could cause undesirable chemical reactions or dryout the vaporization port. In addition, by controlling the electrical energy to the heating elements, the rate of vaporization or the total mass of vaporization can be accurately controlled. In some embodiments, the amount of electrical energy could be optionally varied, and optimized for the specific application. In yet other embodiments, an electrical waveform could be sinusoidal, square wave, or other waveform, which could be optimized for the specific application. In yet other embodiments, the waveform could pulse and cause vaporization, an aerosol or ejections of liquid droplets, and could decrease parasitic heat loss, thereby increasing thermodynamic efficiency.

Figure 9:
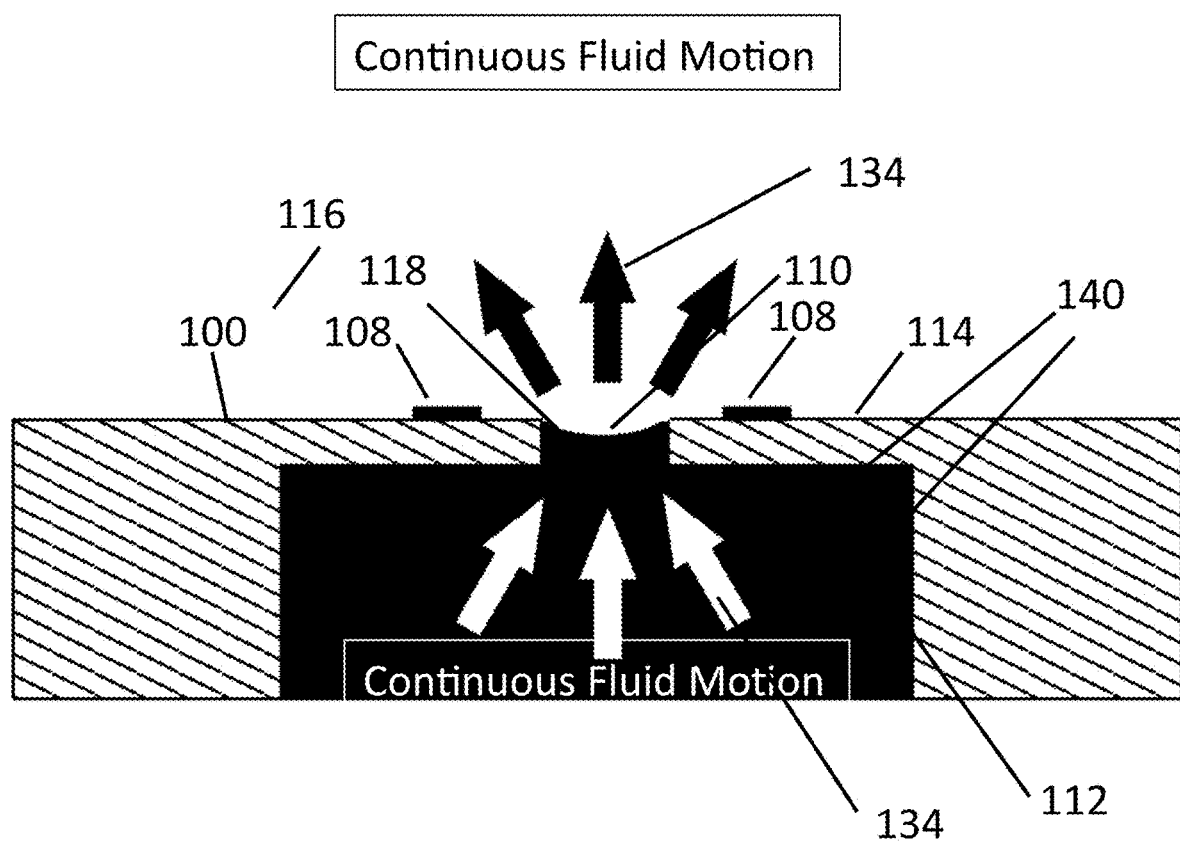
FIG. 9 shows a profile view of the apparatus depicting the major components of an illustrative embodiment.

FIG. 9 refers to an illustrative embodiment where the liquid flows from the liquid source 112 region into the vaporization port 110 and is then vaporized through the meniscus 118 into the surrounding environment 116. In some embodiments, the liquid may be transported from one side (say the backside) of the microfluidic device structure 100, vaporized through meniscus 118 and vapor released from the other side (say the frontside) of the microfluidic device structure 100, such that fluid is transported through the depth of the structure (i.e. though a via or through-hole). In these embodiments, the ability for liquid to travel through the device is made possible because the vaporization port 110 is in fluid communication with the liquid source 112 and the surrounding environment 116. Arrows 134 represent continuous fluid motion from one side of the structure to the other side of the structure. White arrows 134 depict continuous fluid motion of the liquid through the liquid source 112 to vaporization port 110. Black arrows 134 depict continuous fluid motion of the vapor from vaporization port 110 to surrounding environment 116. The ability for fluid to be transported through the depth of the structure can make the vaporization process much more energy efficient. In some embodiments, the ability for fluid to be transported through the depth of the structure can reduce or even prevent dryout, and provide for continuous fluid motion. In some embodiments, this may allow, for example, the heating element 108 be placed in close proximity to vaporization port 110 for desirable thermal communication (e.g. to within 0.5 microns to 1000 microns, or 5 micron to 100 microns) to the meniscus 118, where the phase change occurs. This can dramatically reduce the distance heat must be transferred into the liquid during vaporization, and can allow the heating element 108 to operate at a lower temperature, compared to other vaporizer devices. This can be especially critical because most liquids have low thermal conductivity (for example the thermal conductivity of water is approximately $k_w$=0.58 W/(m K) at room temperature, the thermal conductivity of glycerin is approximately $k_w$=0.29 W/(m K)). The efficient design of these embodiments can also reduce the maximum temperature that the liquid must be exposed to during vaporization. Furthermore, in some embodiments, the more efficient design where the liquid flows through the microfluidic device may significantly reduce dryout of the liquid in the vaporization port 110, providing consistent and superior performance.

FIG. 9 refers to an illustrative embodiment where there is significant contact surface area 140 between the thin structural region 114 and the liquid contained in the vaporization port 110 and the liquid source region 112. Since liquids can have low thermal conductivity, it is important to have a large contact area 140 so that heat can be readily transferred from the thin structural region 114 to the liquid. In some embodiments, the thin structural region 114 may decrease the distance wherein heat may be transferred from the heating element 108 through the thin structural region 114, before reaching the contact area 140 between the thin structural region 114 and the liquid in the liquid source region 112 and vaporization port 110. In some embodiments, having a minimal distance wherein heat is transferred through the thin structural region 114 may be important, because glass has a low thermal conductivity of approximately, $k_g$=1.05 W/(m K). Other materials such as metals, silicon, and the like provide a larger thermal conductivity, for example the thermal conductivity of silicon is approximately $k_{Si}$=130 W/(m K). However, in many embodiments, for thermodynamic efficiency, it is important to keep the thermal energy focused in close proximity to the vaporization ports, and therefore minimize the amount of heat that is transferred to the bulk substrate and surrounding environment. In some embodiments, the thermal energy is substantially confined to vaporization cluster 104. In some embodiments, vaporization cluster 104 can be nominally 1 mm in size. In some embodiments, vaporization cluster 104 can range in size from 100 um to 10 mm. In some embodiments, vaporization cluster 104 can range in size from 10 um to 100 mm. In many of these embodiments, it may be advantageous to use a low thermal conductivity material, such as, but not limited to, a glass, a plastic, a polymer, a fiberglass, a composite, or a ceramic, and the like. In many of these embodiments, the thin structural region 114, combined with a low thermal conductivity material may help to minimize parasitic heat transfer losses to the bulk structure 100 and surrounding environment 116. In yet other embodiments, using an optimized electrical waveform may help to reduce parasitic heat transfer losses to the bulk structure 100 and the surrounding environment 116.

In some embodiments, glass has many features that could make it a suitable structural material for a vaporization device. For example, glass could be made durable, could be available in many geometric forms including thin wafers, could be machined, could be custom blown, shaped or molded, could be widely and commercially available, could be purchased at an affordable price, could be wet etched, could have a low electrical conductivity, could have a low thermal conductivity, could be made hydrophilic with appropriate cleaning processes, could be made hydrophobic with a judiciously chosen surface coating, surfaces could be treated with well-known surface chemistries, could be chemically inert, could be aggressively stripped of organic materials using a Piranha solution, could be mechanically stable below the glass transition temperature, metal could be deposited for electrode leads and heating elements, or could be bonded to itself or to other materials.

In some embodiments, glass could be chosen as a structural material for environmental, toxicity or health reasons. In some embodiments, the electrode leads 116 and the heating elements 108 could be formed from deposition of platinum and titanium. Many other materials could be used for electrode and heating element deposition, such as carbon, gold, silver, nickel, aluminum, and many others. In some embodiments, platinum may be used as electrode leads and resistive heating elements (through Joule heating), and may also be used as Resistive Thermal Devices (RTDs) for measurement of the approximate temperature of the heating elements. The electrical resistance of platinum and many other metals and other materials is a function of temperature, and could be used to determine the approximate temperature of the heating element. In some embodiments, an electrical control circuit could be used for feedback control of vaporization devices, to maintain a constant operating temperature or constant operating power setting, or a temporal profile of operating temperature or operating power, or some arbitrary operating temporal profile that could be tailored for a specific application. Other metals and other materials could be used as RTDs for vaporization devices. However, in some embodiments platinum could be a suitable material. In these embodiments, titanium could be a suitable adhesion material to provide adhesion between a glass substrate and a platinum or other metal deposited film. Other adhesion materials could also be used.

In some embodiments, the heating elements 108 in combination with continuous fluid motion provides steady and uniform heating of the fluid, which may keep the fluid from obtaining an undesirably high temperature, which could cause undesirable chemical by-products, or could combust, partially combust, or otherwise burn scorch, or char the liquid and the microfluidic structure 100. In some embodiments, the continuous fluid motion may provide for a steady operation that may allow the apparatus to continuously function for indefinite periods of time, while minimizing potentially undesirable ramifications, such as liquid dryout, undesirable chemical by-products, scorching or combusting of the liquid, or scorching or combusting of the apparatus.

In some embodiments, vaporization could occur in discrete time periods ranging from a few milliseconds to tens of seconds, or longer. In some embodiments, vaporization could occur in discrete time periods ranging from a few milliseconds to tens of seconds, or longer, to provide precision delivery of vapor mass for accurate dosing.

Figure 10:
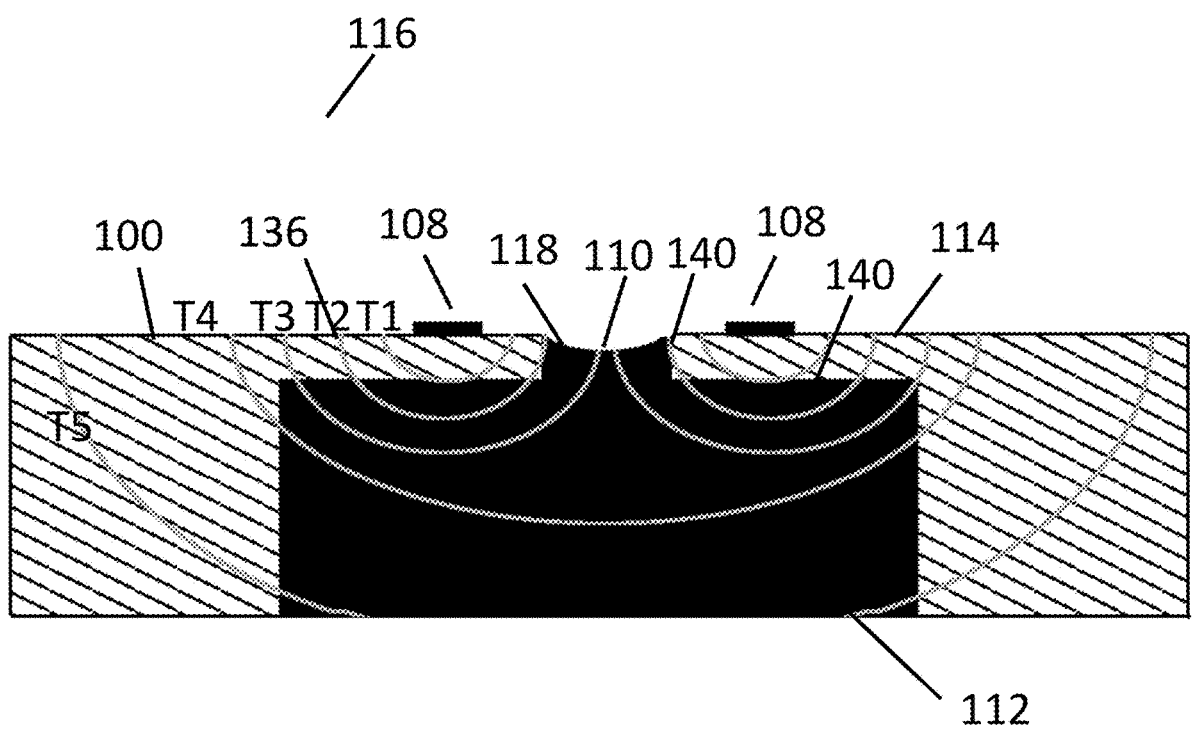
FIG. 10 shows a profile view of the apparatus depicting the major components of an illustrative embodiment.

FIG. 10 shows a profile view of the apparatus depicting the various components of an illustrative embodiment. The surrounding environment 116 is above the structure 100. Vaporization ports 110 are formed in the structure 100 and are in fluid communication with the liquid source region 112 and the surrounding environment 116. A heating element 108 is in thermal communication with the vaporization port 110 and located on a thin structural region 114. The white lines 136 depict contours on constant temperature. In some embodiments, the thin structural region 114 helps to confine thermal energy substantially to within vaporization cluster 104, and to within close proximity of the heating elements 108 and the vaporization ports 110, and thereby reduces thermal losses to the bulk structure 100.

In some embodiments, there is significant contact surface area 140 between the thin structural region 114 and the liquid contained in a vaporization port 110 and the liquid source 112. Since liquids can have low thermal conductivity, it is important to have a large contact area 140 so that heat can be readily transferred from the thin structural region 114 to the liquid. In some embodiments, the thin structural region 114 may decrease the distance wherein heat may be transferred from the heating element 108 through the thin structural region 114, before reaching the contact area 140 between the thin structural region 114 and the liquid in the liquid source region 112 and vaporization port 110. In some embodiments, having a minimal distance wherein heat is transferred through the thin structural region 114 may be desirable, because glass has a low thermal conductivity of approximately, $k_g$=1.05 W/(m K). Other materials such as metals, silicon, and the like provide a larger thermal conductivity, for example the thermal conductivity of silicon is approximately $k_{Si}$=130 W/(m K). However, in many embodiments, for thermodynamic efficiency, it is important to keep the thermal energy focused substantially to within vaporization cluster 104 and within close proximity to the vaporization ports 110, and therefore minimize the amount of heat that is transferred to the bulk substrate 100 and surrounding environment 116. In many of these embodiments, it may be advantageous to use a low thermal conductivity material, such as a glass, a plastic, a polymer, a fiberglass, a composite, or a ceramic, and the like. In many of these embodiments, the thin structural region 114, combined with a low thermal conductivity material may help to minimize parasitic heat transfer losses to the bulk substrate 100 and surrounding environment 116. In yet other embodiments, using an optimized electrical waveform may help to reduce parasitic heat transfer losses to the bulk substrate 100 and the surrounding environment 116.

Figure 11A:
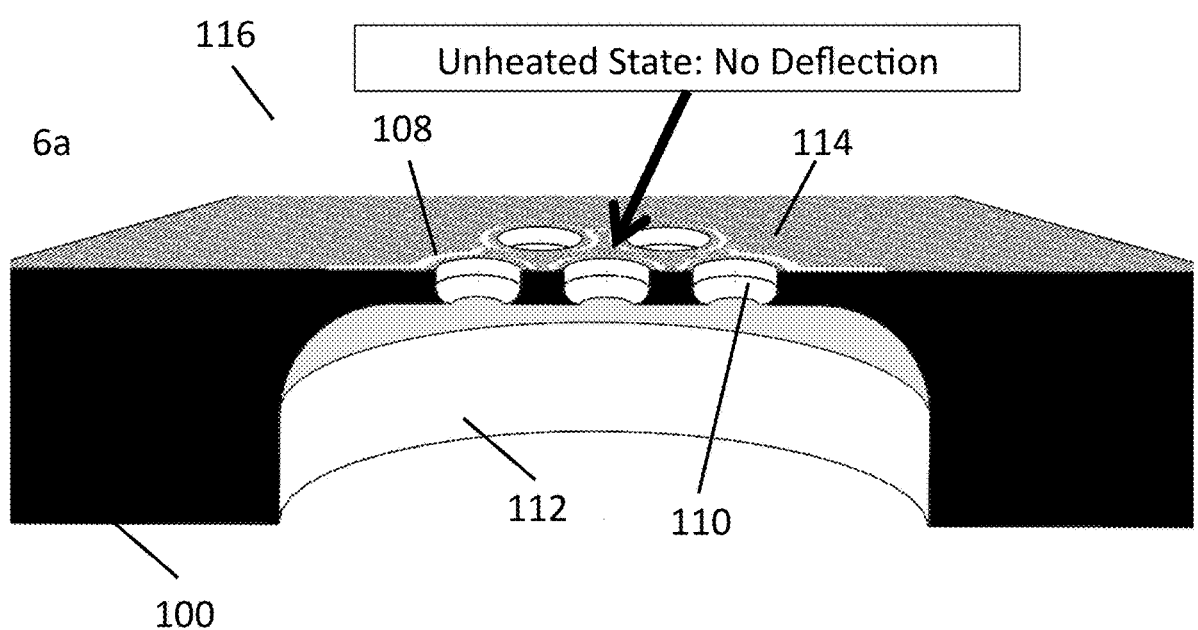
FIGS. 11a and 11b show cross section views of the apparatus depicting the major components of an illustrative embodiment.
Figure 11B:
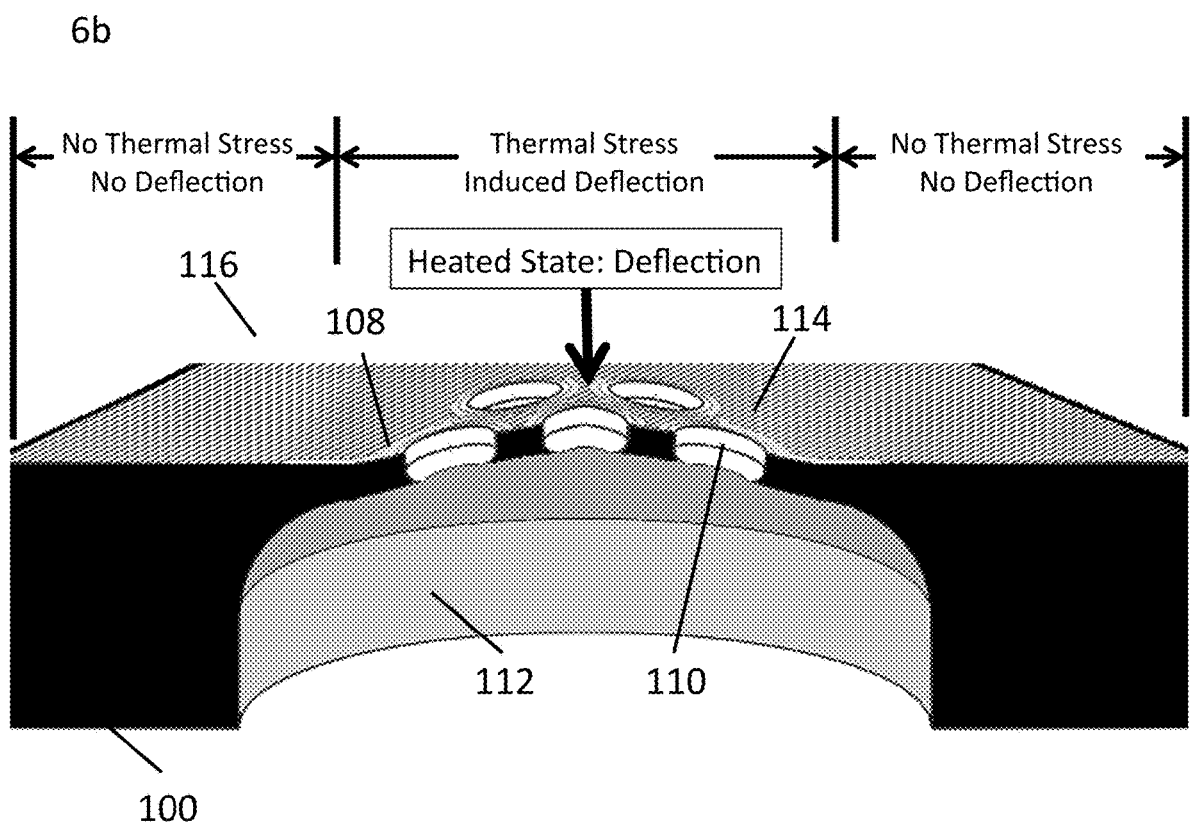

FIGS. 11a and 11b shows a profile view of the apparatus depicting the various components of an illustrative embodiment. The surrounding environment 116 is above the structure 100. Vaporization ports 110 are formed in the structure 100 and are in fluid communication with the liquid source region 112 and the surrounding environment 116. Heating elements 108 are in thermal communication with the vaporization ports 110 and located on a thin structural region 114.

FIG. 11a shows an illustrative embodiment where the thin structural region 114 is in an un-deflected state, which may occur when the apparatus is not being energized. In an embodiment, the heating elements 108 may be energized and produce thermal energy, which could increase the temperature in the proximity of the heating elements 108. The thin structural region 114 in proximity to the heating elements 108 could thermally expand due to an increase in temperature, which could cause thermal stress and/or thermal strain in the thin structural region 114 and in the resistive heating elements 108. In some embodiments, it is desirable for the principal stress to be less than 10-20 MPa. In some embodiments, it is desirable for the principal stress to be less than 70 MPa.

FIG. 11b shows an illustrative embodiment, where a thin structural region 114 is deflected due the thermal expansion, when the heating elements 108 are energized. In an illustrative embodiment, the thin structural region 114, may help confirm the thermal energy to the proximity of the heating element 108, which could help minimize thermal expansion of the bulk structure, and could help to reduce thermal stress and strain in the thin structural region 114. In some embodiments, it is desirable for the principal stress to be less than 10-20 MPa. In some embodiments, it is desirable for the principal stress to be less than 70 MPa.

In an embodiment, the thin structural region 114 could allow for thermal deflection, and could help reduce thermal stress. The mechanical stiffness of a structural beam is proportional to $h^3$, where h is the thickness of the structural beam. In some embodiments, the optionally thin structural region 114, may be sufficiently thin that it could have a relatively low mechanical stiffness, which could allow the thin structural region 114 to deflect with sufficiently low stress, when the heating elements 108 are electrically energized. In some embodiments, it is desirable for the principal stress to be less than 10-20 MPa. In some embodiments, it is desirable for the principal stress to be less than 70 MPa.

In an embodiment, the heating elements 108 could be comprised of metal that has a high coefficient of the thermal expansion, compared to the structural material. The thin structural region 114 may deflect as shown in FIG. 11b, and produce stain on the top surface that could be well-matched to the thermally-induced strain of the heating element 108 material, and thereby could dramatically reduce the stress between heating elements 108 and the thin structural region 114. In some embodiments, it is desirable for the principal stress to be less than 10-20 MPa. In some embodiments, it is desirable for the principal stress to be less than 70 MPa.

Figure 12:
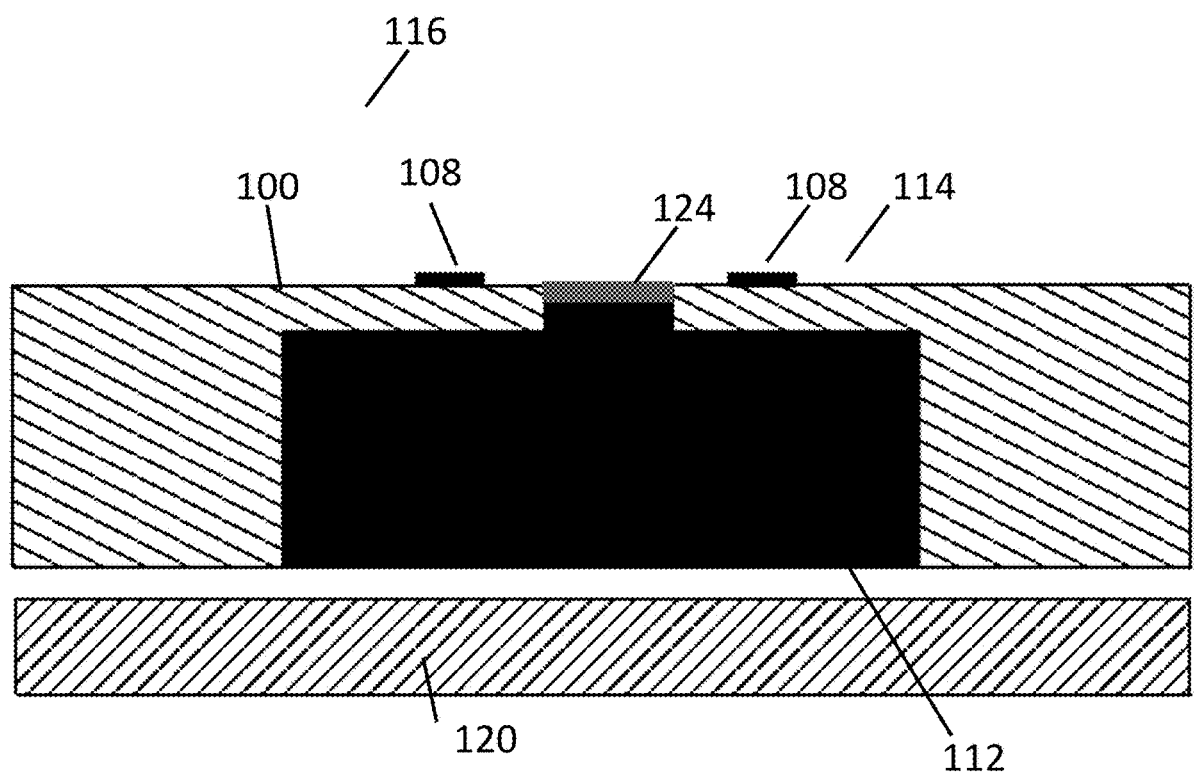
FIG. 12 depicts an illustrative embodiment that has an optional bulk heater or cooler.

FIG. 12 shows a profile view of the apparatus depicting the various components of another illustrative embodiment. In this embodiment, an optional seal 124 could be located between the liquid in the vaporization port 110 and the surrounding environment 116. The seal 124 could be made of a thermally-responsive wax. This could provide a seal to enclose the liquid during storage, and then the optional seal 124 could be vaporized to activate the vaporization apparatus. The optional seal 124 could be used to extend shelf life before the first use, or extend storage life between uses. In some embodiments, the sealing material could be incorporated into the liquid to provide a self-sealing mechanism between uses, or between vaporization processes. The optional seal 124 could be manufactured from many different materials, beyond the exemplary case of wax. In some embodiments, the seal 124 could be comprised of a suitable sealing material which is solid at room temperature but melts, sublimes, recedes, or is cleared from the vaporization port 110 when the vaporizer is active. In some embodiments, the liquid source region 112 could contain a liquid which is a low volatility liquid and the optional seal may not be necessary or may not be desirable. In some embodiments, the surrounding environment 116 could be above the structure. A vaporization port 110 formed in the structure 100 could be in fluid communication with the liquid source region 112, but could be optionally separated from the surrounding environment by the optional seal 124. A heating element 108 could be in close proximity to the vaporization port 110 and located on the thin structural region 114. In some embodiments, heating element 108 is located within 0.5 um-1000 um of vaporization port 110. In some embodiments, heating element 108 is located within 5 um-100 um of vaporization port 110. In some embodiments, the optional seal 124 could be vaporized and allow the liquid in the vaporization port 110 to be in fluid communication with the surrounding environment 116. An optional bulk heater or cooler 120 could be located below the structure 100. This could provide heat that could cause an otherwise solid phase substance to become a liquid, or it could increase the temperature of the bulk liquid so that less thermal energy is required by the heating elements 108. An optional bulk heater or cooler 120 could increase or decrease the bulk temperature of the bulk liquid, and thereby could control the volatility of the liquid before it may undergo vaporization in the vaporization port 110.

Figure 13:
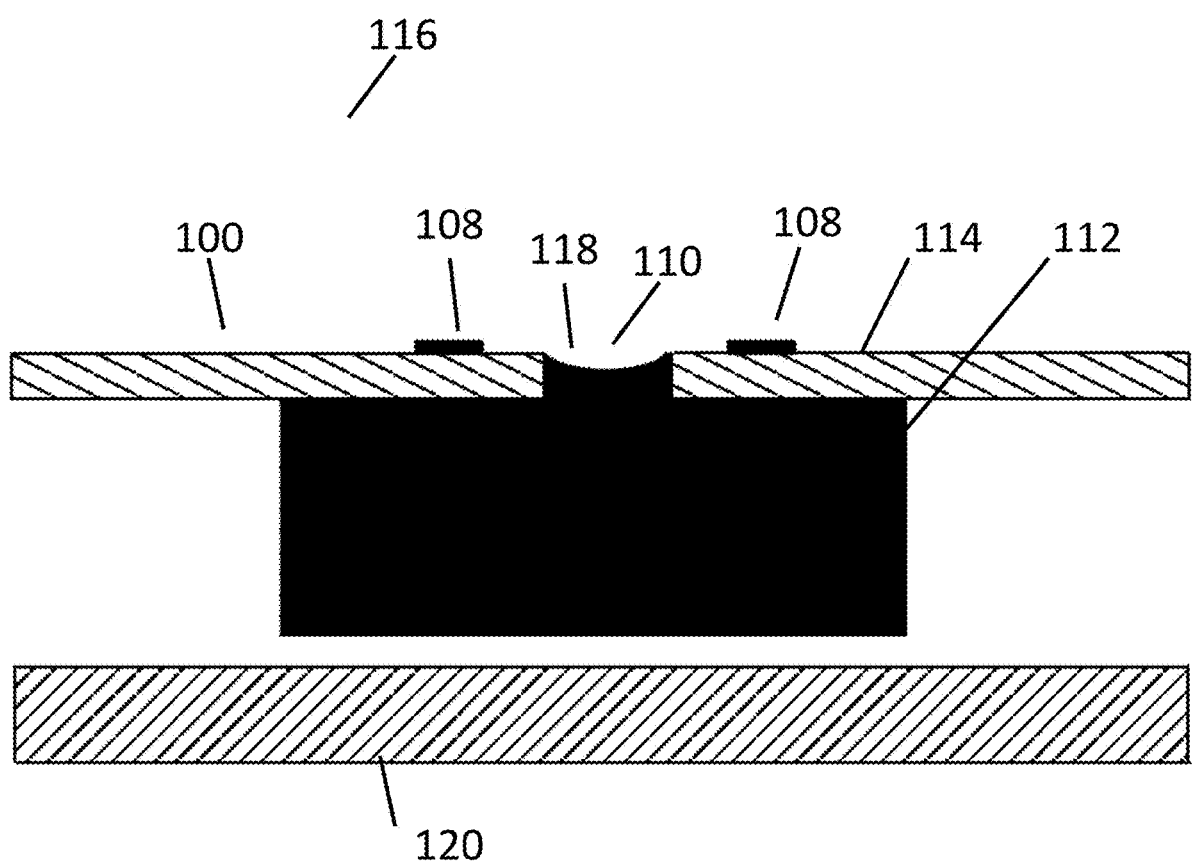
FIG. 13 depicts an illustrative embodiment that has an optional bulk heater or cooler that is shown below the structure.

FIG. 13 shows a schematic of another embodiment where the liquid source region 112 is adjacent to a thin structural region 114. The surrounding environment 116 is above the thin structural region 114. A vaporization port 110 is formed in the structure 100 and is in fluid communication with the liquid source 112 and the surrounding environment 116. A heating element 108 is in thermal communication with the vaporization port 110 and located on a thin structural region 114. An optional bulk heater or cooler 120 is shown below the structure 100.

Figure 14A:
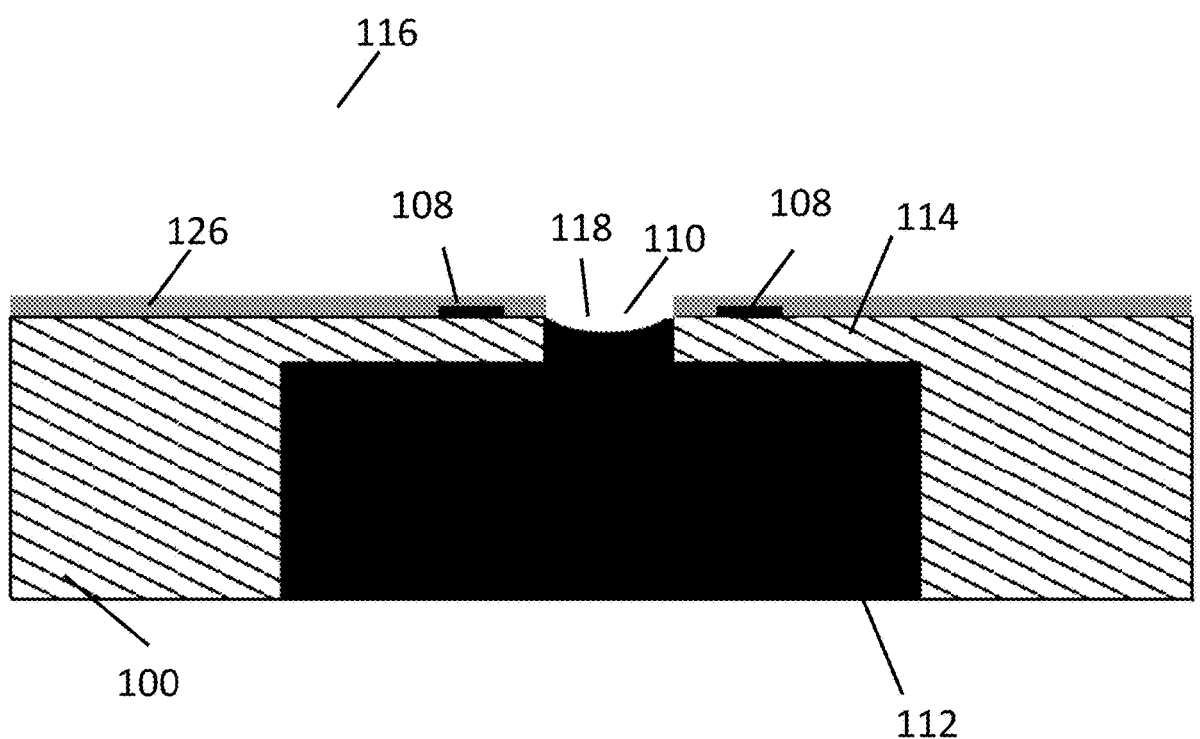
FIGS. 14a, 14b, 14c, and 14d depict various illustrative embodiments of the apparatus.

FIG. 14a shows an illustrative embodiment, where an optional protective layer 126 surrounds the heating element 108. The protective layer 126 could be deposited silicone dioxide, amorphous silicon, silicon nitride, or other material. In some embodiments, the protective layer 126 can protect the heating elements 108 from becoming delaminated, due to differences in thermal expansion between the heating element 108 material and the underlying structural 100 material. In some embodiments, the protective layer 1246 can serve as a chemical and/or electrical barrier between the heating element 108 and the surrounding environment 116. In some embodiments, the protective layer 126 is located in close proximity to the heating element 108. In some embodiments, the protective layer 126 is located within 0.5 um to 1 mm of the heating element 108. In some embodiments the protective layer 126 substantially covers the structure 100.

Figure 14B:
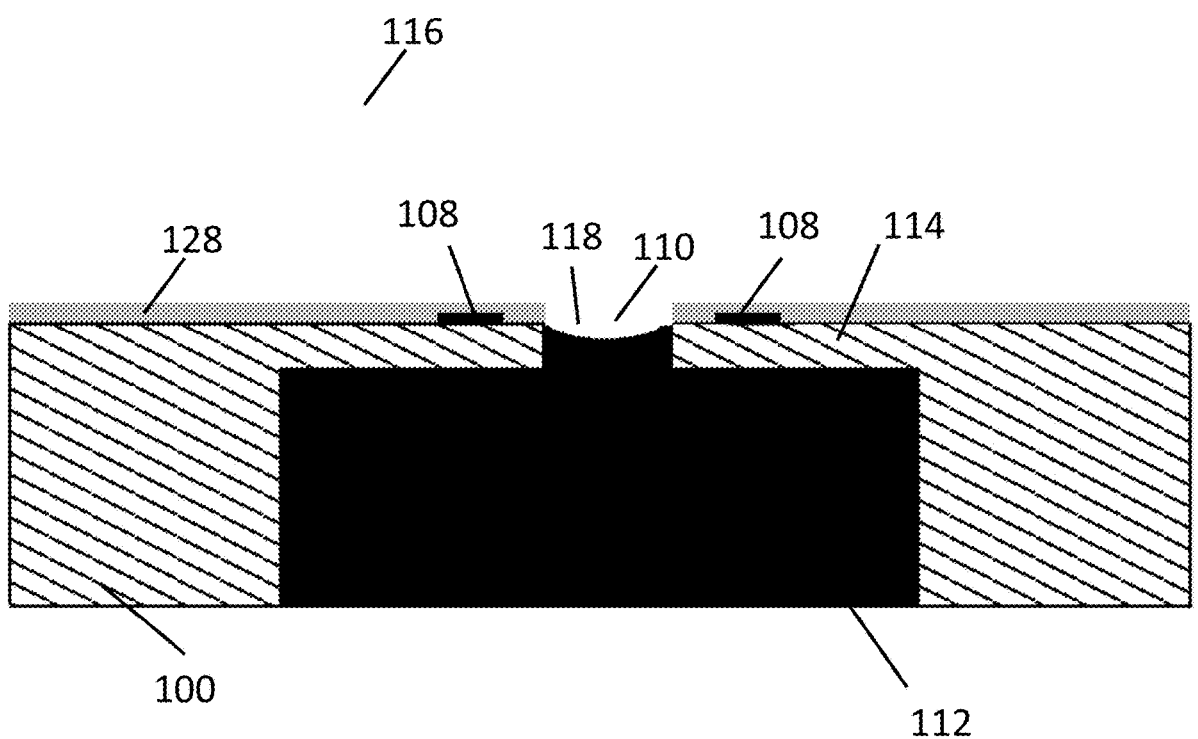

FIG. 14b shows an embodiment where an optional surface coating 128 is coated on the outside of the structure 100, and is located adjacent to the vaporization port 110. I some embodiments it may be desirable to prevent the costing from coating the walls of the vaporization ports 110. Thus when the coating is deposited, the vaporizer ports may be masked off during the coating process. In an embodiment, the optional surface coating 126 is a hydrophobic coating. In another embodiment, the optional surface coating 126 is a hydrophilic coating. In another embodiment, the optional surface coating 126 is a combination of a hydrophobic and a hydrophilic coating. In an embodiment, a hydrophobic coating could be comprised of a fluoropolymer, or other material. In an embodiment, the optional surface coating 126 could be comprised of a chemical monolayer. In an embodiment, a hydrophobic coating could repel hydrophilic liquid and could minimize hydrophilic liquid from wetting the outside of the structure. In an embodiment, a hydrophilic coating could repel hydrophobic liquid and could minimize hydrophobic liquid from wetting the outside of the structure.

Figure 14C:
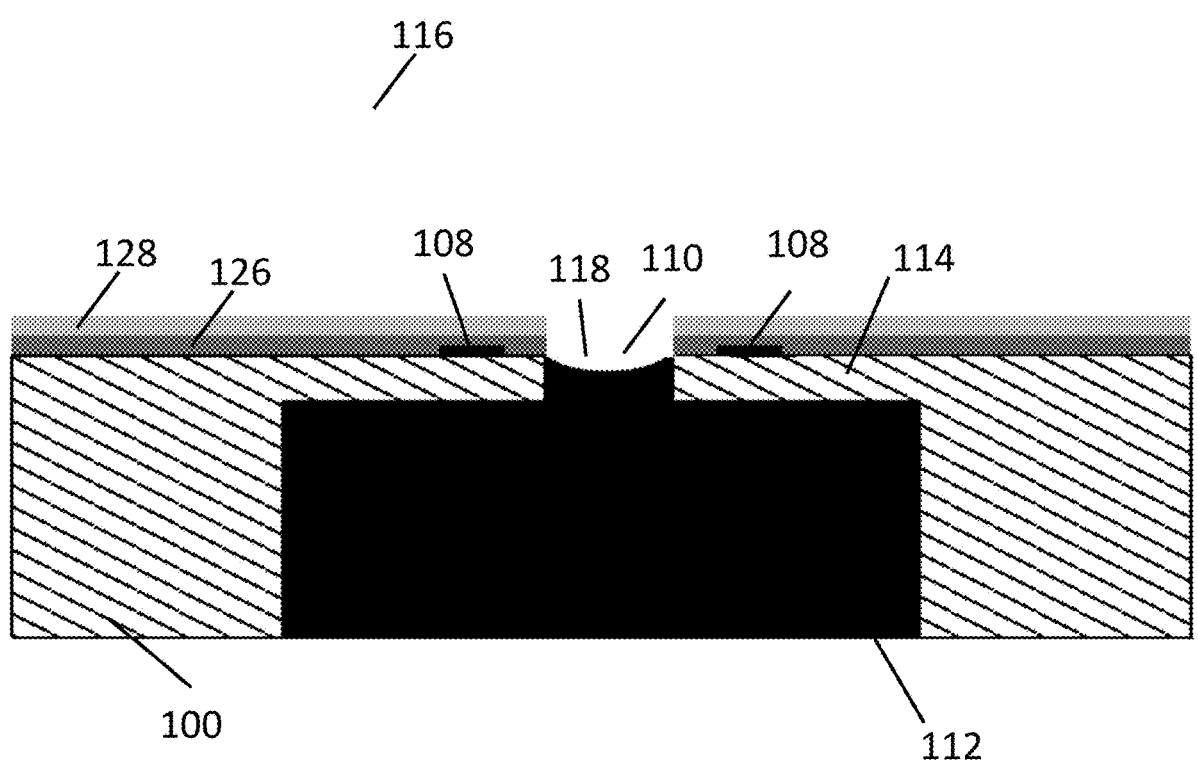

FIG. 14c shows an embodiment where an optional protective layer 126 surrounds the heating element 108, with an optional surface coating 128 that is coated over the optional protective layer 126 that surrounds the heating element 108, and is located adjacent, but optionally not on, the vaporization port 110. The protective layer 126 could be deposited silicone dioxide, amorphous silicon, or other material. In some embodiments, the protective layer 126 can protect the heating elements 108 from becoming delaminated, due to differences in thermal expansion between the heating element 108 material and the underlying structural 100 material. In some embodiments, the protective layer 126 can serve as a chemical and/or electrical barrier between the heating element 108 and the surrounding environment 116. In some embodiments, the protective layer 126 is located in close proximity to the heating element 108. In some embodiments, the protective layer 126 is located within 0.5 um to 1 mm of the heating element 108. In some embodiments the protective layer 126 substantially covers the structure 100. In an embodiment, the surface coating 128 is a hydrophobic coating. In another embodiment, the surface coating 128 is a hydrophilic coating. In another embodiment, the surface coating is a combination of a hydrophobic and a hydrophilic coating. In an embodiment, an optional hydrophobic surface coating 128 could be comprised of a fluoropolymer, or other material. In an embodiment, an optional hydrophobic surface coating 128 could repel hydrophilic liquid and could minimize hydrophilic liquid from wetting the outside of the structure 100. In an embodiment, a hydrophilic surface coating 128 could repel hydrophobic liquid and could minimize hydrophobic liquid from wetting the outside of the structure 100.

Figure 14D:
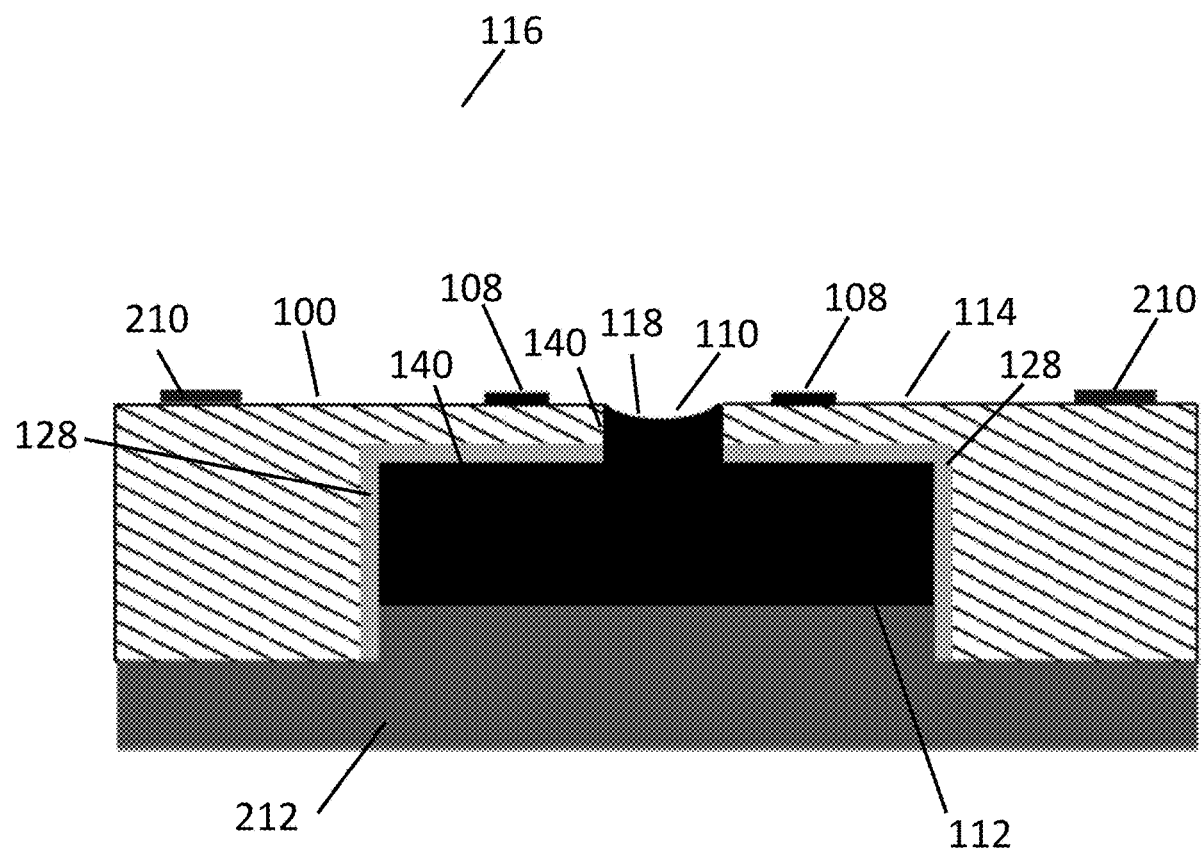

FIG. 14d shows an embodiment where an optional surface coating 128 is coated on the inside of the structure 100, and is located adjacent to the vaporization port 110 and the liquid source region 112. In an illustrative embodiment, the optional surface coating 126 is a hydrophobic coating. A hydrophobic coating can be adapted so that hydrophobic liquids wet the hydrophobic coating. In another embodiment, the optional surface coating 126 is a hydrophilic coating, so that hydrophilic liquids wet the hydrophilic coating. In another embodiment, the optional surface coating 126 is a combination of a hydrophobic and a hydrophilic coating. In an embodiment, a hydrophobic coating could be comprised of a fluoropolymer, or other material. In an embodiment, the optional surface coating 126 could be comprised of a chemical monolayer. In an embodiment, a hydrophobic coating could repel hydrophilic liquid and could minimize hydrophilic liquid from wetting inside the structure 100 and vaporization port 110, while allowing a hydrophobic liquid to wet inside the structure 100 and vaporization port 110. In an embodiment, a hydrophilic coating could repel hydrophobic liquid and could minimize hydrophobic liquid from wetting the inside of the structure 100 and the vaporization port 110.

FIG. 14d shows an illustrative embodiment with an optional structure heater 210 that can be used to apply thermal energy to the structure. The optional structure heater can be a thin film resistive heating element or other type of heating element. Thermal energy from the structure can be used to warm a solid material 212. Solid material 212 can be a solid wax or wax-like substance, or any other type of solid material. The solid material 212 is in thermal communication with structure 100. With the proper application of thermal energy from structure 100, solid material 212 can be controllably melted into a liquid that can occupy liquid source region 112. Optional surface coating 128 can be chosen such that liquid occupying liquid source region 112 can wet structure 100 and vaporization port 110. When heating element 108 is energized, liquid from liquid source 112 can be vaporized in vaporization port 110, such that vapor can be emitted into the surrounding environment 116.

The embodiments described herein are exemplary. Modifications, rearrangements, substitute processes, materials, etc. may be made to these embodiments and still be encompassed within the teachings set forth herein.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "an element configured to carry out recitations A, B and C" can include a first element configured to carry out recitation A working in conjunction with a second elements configured to carry out recitations B and C.

While the above detailed description has shown, described, and pointed out novel features as applied to illustrative embodiments, it will be understood that various omissions, substitutions, and changes in the form and details of the devices or methods illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A vaporization apparatus that is placed within a surrounding environment to vaporize liquid into the surrounding environment, comprising;
    at least one liquid source;
    a plurality of vaporization ports formed in a planar structure comprising a through hole, the through hole with lateral dimensions ranging from 10 um to 300 um, that is in fluid communication with the liquid source on a first side and the surrounding environment on a second side, wherein fluid is transported from the first side of the structure to the second side of the structure through the through hole;
    at least one planar heating element formed on the second side of the planar structure and disposed around a plurality of vaporization ports, wherein
    the at least one planar heating element and the plurality of vaporization ports are microfabricated,
    the dimension of the vaporization ports and the planar structure materials are selected to wick liquid from the liquid source by surface tension, and
    heat applied from the heating element, through the planar structure to liquid that is in direct contact with the planar structure, vaporizes the liquid thereby releasing vapor through the vaporization ports into the surrounding environment, wherein
    the liquid source comprises liquid melted from a solid material by application of heat to the solid material from the planar structure.

2. Apparatus of claim 1, wherein the fluid communication between the liquid source and the surrounding environment occurs throughout the depth of the apparatus.

3. Apparatus of claim 1 wherein the structure comprises a thin structural region, with a thickness varying from 1 um to 100 um.

4. Apparatus of claim 2, wherein a protective layer is formed on the structure that surrounds the heating element.

5. Apparatus of claim 3, wherein the protective layer comprises deposited glass.

6. Apparatus of claim 2, wherein a surface coating is formed on the structure but masked from forming on the walls of the vaporization ports.

7. Apparatus of claim 5, wherein the surface coating comprises fluoropolymers.

8. Apparatus of claim 3, wherein a surface coating is formed on the structure but masked from forming on the walls of the vaporization ports.

9. Apparatus of claim 1, wherein the heating element is a thin-film resistive heating element.

10. Apparatus of claim 8, wherein the resistances of the resistive heating elements are varied to provide a controlled thermal distribution.

11. Apparatus of claim 9, wherein the resistive heating elements, are electrically connected in parallel and series combination.

12. A method for vaporizing liquid into the surrounding environment, comprising;
    forming a plurality of vaporization ports, wherein the vaporization ports are comprised of a through hole in a planar structure, the holes with lateral dimensions varying from 10 um to 300 um, and are in fluid communication with the liquid on a first side and the surrounding environment on a second side;
    selecting the dimension of the ports and the planar structure materials to enable wicking of liquid from the liquid source by surface tension;
    wicking the liquid from a liquid source;
    applying heat from at least one planar heating element through the planar structure to the liquid that is in direct contact with the planar structure with the at least one planar heating element disposed around a plurality of vaporization ports, and;
    releasing vaporized liquid from the vaporization ports into the surrounding environment so that fluid is transported from the first side of the planar structure to the second side of the planar structure through the through hole wherein,
the at least one planar heating element and the plurality of vaporization ports are microfabricated, wherein
    the liquid source comprises liquid melted from a solid material by application of heat to the solid material from the planar structure.

13. Method of claim 11, wherein during operation, liquid continuously flows from the liquid source to the vaporization port, changes phase from liquid to vapor, and the vapor continuously flows from the vaporization port to the surrounding environment.

14. Method of claim 12, wherein a thin structural region substantially confines thermal energy to close proximity of the at least one heating element and the at least one vaporization port.

15. Method of claim 13, wherein the thin structural region reduces thermally-induced stresses that occur in close proximity to the at least one heating element and the at least one vaporization port.

16. Apparatus of claim 1 wherein the vaporization ports are arranged in clusters of seven ports.

* * * * *